United States Patent [19]

Braestrup et al.

[11] Patent Number: 5,010,077

[45] Date of Patent: Apr. 23, 1991

[54] β-CARBOLIN-3-CARBOXYLIC ACID DERIVATIVES USEFUL FOR TREATING ANXIETY AND RELATED DISORDERS

[75] Inventors: Claus T. Braestrup, Gentofte; Mogens C. Nielsen, Roskilde; Joergen A. Christensen, Virum; Mogens Engelstoft, Vaerloese; Henning Schou, Copenhagen, all of Denmark; Ulrich Eder, Berlin, Fed. Rep. of Germany; Günter Neef, Berlin, Fed. Rep. of Germany; Andreas Huth, Berlin, Fed. Rep. of Germany; Dieter Rahtz, Berlin, Fed. Rep. of Germany; Ralph Schmiechen, Berlin, Fed. Rep. of Germany

[73] Assignees: A/S Ferrosan, Soeborg, Denmark; Schering Aktiengesellschaft, Berlin and Bergkamen, Fed. Rep. of Germany

[21] Appl. No.: 188,145

[22] Filed: Apr. 25, 1988

Related U.S. Application Data

[60] Continuation of Ser. No. 731,244, May 7, 1985, abandoned, which is a continuation of Ser. No. 433,308, Oct. 7, 1982, abandoned, which is a division of Ser. No. 182,244, Aug. 28, 1980, Pat. No. 4,731,536.

[30] Foreign Application Priority Data

Aug. 29, 1979 [DK] Denmark ............................ 3622/79
Feb. 29, 1980 [DK] Denmark ............................ 889/80
Apr. 22, 1980 [DE] Fed. Rep. of Germany ....... 3015816
Jun. 20, 1980 [DE] Fed. Rep. of Germany ....... 3023567

[51] Int. Cl.$^5$ ................. C07D 471/04; A61K 31/535
[52] U.S. Cl. ............................... 514/228.8; 514/232.8; 514/253; 514/292; 546/85; 546/86; 546/87; 544/126; 544/361
[58] Field of Search ................ 546/85, 86, 87; 544/126, 361; 514/292, 253, 232.8, 228.8

[56] References Cited

U.S. PATENT DOCUMENTS

| | | | |
|---|---|---|---|
| 4,371,536 | 2/1983 | Braestrup et al. | 514/292 |
| 4,435,403 | 3/1984 | Braestrup et al. | 514/292 |
| 4,596,808 | 6/1986 | Braestrup et al. | 514/292 |
| 4,600,715 | 7/1986 | Huth et al. | 514/222 |
| 4,631,285 | 12/1986 | Petersen et al. | 514/292 |
| 4,644,062 | 2/1987 | Haffer et al. | 546/85 |
| 4,645,773 | 2/1987 | Engelstoft et al. | 514/292 |

FOREIGN PATENT DOCUMENTS 786351 5/1968 Canada .................................. 546/85

OTHER PUBLICATIONS

Chem. Abstracts, vol. 58, (12), pp. 12,521(h) to 12,522-d, Jun. 10, 1963.

Primary Examiner—Alan L. Rotman
Attorney, Agent, or Firm—Millen, White & Zelano

[57] ABSTRACT

A β-carbolin-3-carboxylic acid derivative of the formula

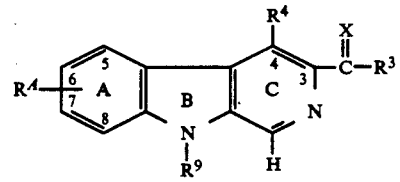

wherein:

X is oxygen, sulphur or $NR^{10}$, wherein $R^{10}$ is hydrogen, $C_{1-6}$-alkyl, $C_{1-6}$-alkenyl, $C_{3-7}$-cycloalkyl or $C_{3-7}$-cycloalkenyl;

$R^3$ is (a) $C_{1-10}$-alkoxy, $C_{1-10}$-alkenyloxy, $C_{6-10}$-aryloxy, $C_{7-11}$-aralkoxy or $C_{8-12}$-aralkenyloxy, each optionally substituted with one or more hydroxy groups, halogen atoms, $CF_3$ groups, $C_{1-10}$-alkoxy groups or $C_{2-4}$-alkenyloxy groups or each optionally substituted with an amino, di-$C_{1-6}$-alkylamino, $C_{1-10}$-alkoxycarbonyl or $C_{1-10}$-alkenyloxycarbonyl group; or (b) $NR^{11}R^{12}$, wherein $R^{11}$ and $R^{12}$ are the same or different and each is (i) hydrogen, (ii) hydroxy, (iii) $C_{1-10}$-alkyl, (iv) $C_{2-10}$-alkenyl, (v) $C_{6-10}$-aryl, (vi) $C_{7-11}$-aralkyl, (vii) $C_{8-12}$-aralkenyl, (viii) $C_{3-7}$-cycloalkyl, or (ix) $C_{3-7}$-cycloalkenyl, each of groups (iii)–(ix) optionally substituted with hydroxy, carboxamido, carboxy, $C_{1-10}$-alkoxycarbonyl or $C_{1-10}$-alkenyloxycarbonyl; or (x) amino optionally substituted with $C_{1-10}$-alkyl, $C_{2-10}$-alkenyl, $C_{6-10}$-aryl, $C_{7-11}$-aralkyl, $C_{8-12}$-aralkenyl, $C_{3-7}$-cycloalkyl or $C_{3-7}$-cycloalkenyl; or wherein $R^{11}$ and $R^{12}$ together with the connecting nitrogen atom form a 5-, 6- or 7-membered heterocyclic ring, which may also contain one additional N or one O atom, and which may be optionally substituted with the same groups of substituents listed for groups (iii)–(ix) above, with the proviso that $R^{11}$ and $R^{12}$ cannot both be hydroxy; or wherein X and $R^3$ together represent a single nitrogen atom;

$R^4$ is hydrogen, $C_{1-10}$-alkyl, $C_{2-10}$-alkenyl, $C_{3-7}$-cycloalkyl, $C_{3-7}$-cycloalkenyl, $C_{7-10}$-aralkyl, $C_{8-10}$-aralkenyl, phenyl, $C_{7-10}$-alkoxyphenyl or $C_{8-10}$-alkenyloxyphenyl;

$R^A$ is F, Cl, Br, I, $NO_2$, $NR^{13}R^{14}$, $NHCOR^{13}$, CN, $COOR^{13}$, $OR^{13}$, $SCH_3$ or $SO_2NR^{11}R^{12}$, wherein $R^{13}$ and $R^{14}$ each is hydrogen or $C_{1-6}$-alkyl optionally substituted with hydroxy or halogen; and wherein $R^{11}$ and $R^{12}$ are as defined above, and wherein there may be 1–4 identical or different $R^A$'s; and $R^9$ is hydrogen, $C_{1-8}$-alkyl, $C_{1-8}$-alkenyl, $C_{1-8}$-alkoxycarbonyl, $C_{1-8}$-alkenyloxycarbonyl, or $C_{1-8}$-alkenyloxy;

with the proviso that $R^{11}$ and $R^{12}$ are not both hydrogen, when X is oxygen and when $R^4$, $R^A$ and $R^9$ each is hydrogen; that one of $R^{11}$ and $R^{12}$ is not hydrogen when the other is amino and when X is oxygen and $R^4$, $R^A$ and $R^9$ each are hydrogen; and that $R^4$, $R^A$ and $R^9$ each is not hydrogen when X is oxygen and $R^3$ is $OCH_3$.

have valuable pharmacological properties.

15 Claims, No Drawings

β-CARBOLIN-3-CARBOXYLIC ACID DERIVATIVES USEFUL FOR TREATING ANXIETY AND RELATED DISORDERS

This application is a continuation of application Ser. No. 731,244 filed May 7, 1985 abandoned which is a continuation of Ser. No. 433,308 filed Oct. 7, 1982 abandoned which is a divisional of Ser. No. 182,244 filed Aug. 28, 1980, now U.S. Pat. No. 4,731,536.

BACKGROUND OF THE INVENTION

This invention relates to new β-carbolin-3-carboxylic acid derivatives, and to methods of preparing them.

The specification of Canadian Patent Number 786,351 discloses β-carbolin-3-carboxylic acid amides derivatives substituted in the 1-position by alkyl containing no more than 5 carbon atoms, trifluoromethyl, phenyl or benzyl, as well as two specific compounds having no substituent at the 1-position, viz. β-carbolin-3-carbohydrazide and β-carbolin-3-carboxylic acid amide.

Danish Patent Specification Number 98,436 discloses a method of preparing methyl β-carbolin-3-carboxylate.

SUMMARY OF THE INVENTION

It is an object of this invention to provide new compounds having pharmacological activity as well as a method of using them.

Upon further study of the specification and appended claims, further objects and advantages of this invention will become apparent to those skilled in the art.

These objects have been attained by providing novel β-carbolin-3-carboxylic acid derivatives of Formula I

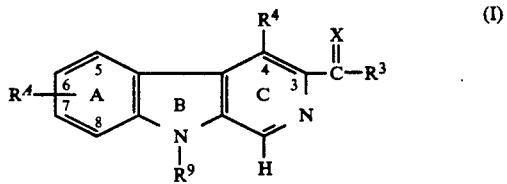

wherein

X is oxygen, sulphur or $NR^{10}$, wherein $R^{10}$ is hydrogen, lower alkyl or cycloalkyl;

$R^3$ is (a) alkoxy, aryloxy or aralkoxy, each optionally substituted with one or more, e.g., 1–3, halogen atoms (F, Cl, Br, I), hydroxy groups, $CF_3$ groups, or alkoxy groups or with an amino, dialkylamino or alkoxycarbonyl group; or (b) $NR^{11}R^{12}$, wherein $R^{11}$ and $R^{12}$ are the same or different and each is (i) hydrogen (ii) hydroxy, (iii) alkyl, (iv) aryl, (v) aralkyl or (vi) cycloalkyl, the latter four (iii–vi) optionally substituted with a hydroxy, a carboxamido, an alkoxycarbonyl, a carboxy, a monosaccharide or a heterocyclic group, or (vii) amino optionally substituted with alkyl, aryl, aralkyl, or cycloalkyl; or wherein $R^{11}$ and $R^{12}$ together with the adjoining nitrogen atom form an optionally substituted 5-, 6- or 7-membered heterocyclic ring; with the proviso that $R^{11}$ and $R^{12}$ cannot both be hydroxy; or wherein X and $R^3$ together represent a single nitrogen atom;

$R^4$ is hydrogen, alkyl, cycloalkyl, aralkyl, phenyl, or an alkoxyphenyl group containing up to 10 carbon atoms, $R^4$ is $R^{13}$ F, Cl, Br, I, $NO_2$, $NR^{13}R^{14}$, $NHCOR^{13}$, CN, $COOR^{13}$, $OR^{13}$, $SCH_3$ or $SO_2NR^{11}R^{12}$; wherein $R^{13}$ and $R^{14}$ each is hydrogen or alkyl containing up to 6 carbon atoms and optionally substituted with hydroxy or halogen (F, Cl, Br, I) and wherein $R^{11}$ and $R^{12}$ are as defined above and wherein there may be 1–4 identical or different $R^4$s; and $R^9$ is hydrogen, alkyl or alkoxycarbonyl each of the latter three containing up to 8 carbon atoms; with the provisos:

that $R^{11}$ and $R^{12}$ cannot both be hydrogen, when X is oxygen and when $R^4$, $R^4$ and $R^9$ each is hydrogen, that one of the substituents $R^{11}$ and $R^{12}$ cannot be hydrogen when the other is amino and when X is oxygen and $R^4$, $R^4$ and $R^9$ each is hydrogen, and that $R^4$, $R^4$ and $R^9$ each cannot be hydrogen when X is oxygen and $R^3$ is $OCH_3$.

These new compounds possess valuable pharmacological properties. In particular, they act on the central nervous system and are suitable for use in psychopharmaceutical preparations.

DETAILED DISCUSSION

Unless otherwise defined herein, the terms "alkyl", "aryl", "aralkyl", "alkoxy", "aryloxy" and "aralkoxy" are used herein to define saturated or unsaturated, straight-chain or branched, or ring groups, as appropriate, containing up to 10 carbon atoms. The terms "lower alkyl" and "lower alkoxy" are used herein to define saturated or unsaturated, straight-chain or branched groups containing up to 6 carbon atoms. Thus, the alkyl moieties throughout this specification, in general, refer to aliphatic hydrocarbon groups, including alkyl, alkenyl and alkynyl groups. The term "cycloalkyl" is used herein to define groups containing from 3 to 7 carbon atoms, e.g., $C_{3-7}$-cycloalkyl or -cycloalkenyl per the above. Suitable aryl groups include phenyl and naphthyl. For each of the $C_{1-10}$ groups mentioned above, the preferred carbon atom range is 1–6. For the $C_{1-6}$-alkyl and -alkoxy groups, 1–2 carbon atoms are preferred. Preferred $C_{3-7}$ cyclo groups have 5–6 carbon atoms. For the $R^9$ groups, 1–7 carbon atoms are preferred. It is also preferred that the A ring contain 1 or 2 $R^4$'s, preferably 1.

When $R^{11}$ and $R^{12}$ together form a 5-, 6- or 7-membered hetero ring with the connecting N-atom, they represent a corresponding $C_4$, 5 or 6-alkylene chain, wherein one of the carbon atoms can be replaced by an N or O atom. These hetero rings can also be substituted by one or more of the substituents mentioned above for $R^{11}$, $R^{12}$ groups (iii)–(vi), preferably on the second N atom of those rings containing 2 hetero N atoms.

As mentioned above, monosaccharide and heterocyclic groups can be substituents on the groups (iii)–(vi) for $R^{11}$ and $R^{12}$. They are thus equivalents of the hydroxy, carboxamido and alkoxycarbonyl substituents when so used for this purpose. Suitable monosaccharides have 5–6 carbon atoms and include polyhydroxy aldehydes (aldoses) and polyhydroxy ketones (ketoses). Examples of monosaccharides are arabinose, xylose, ribulose, glucose, mannose, galactose, rhamnose and 2-desoxyribose.

Suitable heterocycles have 5–10 ring atoms and 1–2 hetero atoms selected from O, N and S, preferably 1 hetero atom. Examples of heterocyclic groups are pyridyl, N-oxo-pyridyl, furyl, thienyl, thiazolyl, oxazolyl, isothiazolyl, imidazolyl, pyrimidyl, pyrazyl, pyridazyl, thiadiazolyl, quinolyl, isoquinolyl, 5,6,7-8-tetrahydroquinolyl, benzimidazolyl and benzthiazolyl.

Preferred compounds of Formula I are those in which X is oxygen, $R^3$ is saturated alkoxy, $R^4$ is lower saturated alkyl or cycloalkyl or phenyl and $R^4$ and $R^9$ are hydrogen.

Examples of such compounds include:
4-methyl-β-carbolin-3-carboxylic acid ethyl ester,
4-ethyl-β-carbolin-3-carboxylic acid ethyl ester,
4-n-propyl-β-carbolin-3-carboxylic acid ethyl ester,
4-iso-propyl-β-carbolin-3-carboxylic acid ethyl ester,
4-n-butyl-β-carbolin-3-carboxylic acid ethyl ester,
4-cyclopentyl-β-carbolin-carboxylic acid ethyl ester,
4-cyclohexyl-β-carbolin-3-carboxylic acid ethyl ester,
4-phenyl-β-carbolin-3-carboxylic acid ethyl ester,
4-p-methoxyphenyl-β-carbolin-3-carboxylic acid ethyl ester,
4-pentyl-β-carbolin-3-carboxylic acid ethyl ester,
4-methyl-β-carbolin-3-carboxylic acid-2'-hydroxyethyl ester,
4-methyl-β-carbolin-3-carboxylic acid methyl ester,
4-methyl-β-carbolin-3-carboxylic acid n-propyl ester,
4-ethyl-β-carbolin-3-carboxylic acid methyl ester,
4-ethyl-β-carbolin-3-carboxylic acid n-propyl ester,
4-ethyl-β-carbolin-3-carboxylic acid iso-propyl ester,
4-n-propyl-β-carbolin-3-carboxylic acid methyl ester,
4-n-propyl-β-carbolin-3-carboxylic acid n-propyl ester,
4-n-propyl-β-carbolin-3-carboxylic acid 2'-hydroxyethyl ester,
4-iso-propyl-β-carbolin-3-carboxylic acid methyl ester,
4-iso-propyl-β-carbolin-3-carboxylic acid n-propyl ester,
4-iso-propyl-β-carbolin-3-carboxylic acid iso-propyl ester,
4-n-butyl-β-carbolin-3-carboxylic acid methyl ester,
4-n-butyl-β-carbolin-3-carboxylic acid 2'-hydroxyethyl ester,
4-n-butyl-β-carbolin-3-carboxylic acid n-propyl ester,
4-cyclohexyl-β-carbolin-3-carboxylic acid methyl ester,
4-cyclohexyl-β-carbolin-3-carboxylic acid propyl ester,
4-phenyl-β-carbolin-3-carboxylic acid methyl ester,
4-phenyl-β-carbolin-3-carboxylic acid n-propyl ester,
4-phenyl-β-carbolin-3-carboxylic acid iso-propyl ester,
4-phenyl-β-carbolin-3-carboxylic acid n-butyl ester,
4-phenyl-β-carbolin-3-carboxylic acid 2'-hydroxyethyl ester, and
4-n-pentyl-β-carbolin-3-carboxylic acid methyl ester.

Another group of preferred compounds is the β-carbolin-3-carboxylic acid amides wherein $R^4$ is lower saturated alkyl or cycloalkyl or phenyl and $R^4$ and $R^9$ are hydrogen.

Examples of such compounds include:
4-methyl-β-carbolin-3-carboxamide,
N,4-dimethyl-β-carbolin-3-carboxamide,
N,N,4-trimethyl-β-carbolin-3-carboxamide,
4-ethyl-β-carbolin-3-carboxamide,
4-ethyl-β-carbolin-3-carboxylic acid N-methyl amide,
4-n-propyl-β-carbolin-3-carboxylic acid N-methyl amide,
4-iso-propyl-β-carbolin-3-carboxylic acid N-methyl amide,
4-n-butyl-β-carbolin-3-carboxylic acid N-methyl amide,
4-cyclohexyl-β-carbolin-3-carboxylic acid N-methyl amide,
4-phenyl-β-carbolin-3-carboxamide,
4-phenyl-β-carbolin-3-carboxylic acid N-methyl amide,
4-phenyl-β-carbolin-3-carboxylic acid N,N-dimethyl amide, and
4-phenyl-β-carbolin-3-carboxylic acid N-ethyl amide.

A further group of preferred compounds comprises those having one or more substituents on the A-ring.

Examples of such compounds include:
6-fluoro-β-carbolin-3-carboxylic acid ethyl ester,
7-nitro-β-carbolin-3-carboxylic acid ethyl ester,
5-methyl-β-carbolin-3-carboxylic acid ethyl ester,
8-methyl-β-carbolin-3-carboxylic acid ethyl ester,
7-fluoro-β-carbolin-3-carboxylic acid ethyl ester,
8-fluoro-β-carbolin-3-carboxylic acid ethyl ester,
5-cyano-β-carbolin-3-carboxylic acid ethyl ester,
5-chloro-β-carbolin-3-carboxylic acid ethyl ester,
7-chloro-β-carbolin-3-carboxylic acid ethyl ester,
8-chloro-β-carbolin-3-carboxylic acid ethyl ester,
5-nitro-β-carbolin-3-carboxylic acid ethyl ester,
6-cyano-β-carbolin-3-carboxylic acid ethyl ester,
5-methoxy-β-carbolin-3-carboxylic acid ethyl ester,
6-methoxy-β-carbolin-3-carboxylic acid ethyl ester,
7-methoxy-β-carbolin-3-carboxylic acid ethyl ester,
8-fluoro-β-carbolin-3-carboxylic acid ethyl ester,
6-fluoro-4-methyl-β-carbolin-3-carboxylic acid ethyl ester,
5-chloro-6-methoxy-β-carbolin-3-carboxylic acid ethyl ester,
4,6-dimethyl-β-carbolin-3-carboxylic acid ethyl ester,
4-ethyl-6-methyl-β-carbolin-3-carboxylic acid ethyl ester,
6-methyl-4-phenyl-β-carbolin-3-carboxylic acid ethyl ester,
4-ethyl-6-fluoro-β-carbolin-3-carboxylic acid ethyl ester,
6-fluoro-4-phenyl-β-carbolin-3-carboxylic acid ethyl ester,
6-fluoro-β-carbolin-3-carboxylic acid N-methylamide,
6-methoxy-β-carbolin-3-carboxylic acid N-methylamide,
7-nitro-β-carbolin-3-carboxylic acid N-methylamide,
6-carbethoxy-β-carbolin-3-carboxylic acid ethyl ester,
7-cyano-β-carbolin-3-carboxylic acid ethyl ester,
5-carbethoxy-β-carbolin-3-carboxylic acid ethyl ester,
5-hydroxymethyl-β-carbolin-3-carboxylic acid ethyl ester,
6-chloro-β-carbolin-3-carboxylic acid ethyl ester,
6-bromo-β-carbolin-3-carboxylic acid ethyl ester,
6-bromo-4-methyl-β-carbolin-3-carboxylic acid ethyl ester,
6-bromo-4-ethyl-β-carbolin-3-carboxylic acid ethyl ester,
6-bromo-4-phenyl-β-carbolin-3-carboxylic acid ethyl ester,
6-bromo-4-methyl-β-carbolin-3-carboxylic acid methyl ester,
6-bromo-4-phenyl-β-carbolin-3-carboxylic acid methyl ester,
6-bromo-4-methyl-β-carbolin-3-carboxylic acid n-propyl ester,
6-chloro-4-methyl-β-carbolin-3-carboxylic acid ethyl ester,
6-chloro-4-ethyl-β-carbolin-3-carboxylic acid ethyl ester,
6-chloro-4-phenyl-β-carbolin-3-carboxylic acid ethyl ester,
6-chloro-4-methyl-β-carbolin-3-carboxylic acid methyl ester,
6-chloro-4-phenyl-β-carbolin-3-carboxylic acid methyl ester,
6-chloro-4-phenyl-β-carbolin-3-carboxylic acid n-propyl ester, 6-chloro-4-methyl-β-carbolin-3-carboxylic acid i-propyl ester,
6-methoxy-4-methyl-β-carbolin-3-carboxylic acid methyl ester,
4-ethyl-6-methoxy-β-carbolin-3-carboxylic acid methyl ester,
6-methoxy-4-phenyl-β-carbolin-3-carboxylic acid methyl ester,
6-methoxy-4-methyl-β-carbolin-3-carboxylic acid ethyl ester,
4-ethyl-6-methoxy-β-carbolin-3-carboxylic acid n-propyl ester,
6-methoxy-4-phenyl-β-carbolin-3-carboxylic acid ethyl ester,
6-ethoxy-4-methyl-β-carbolin-3-carboxylic acid ethyl ester,
6-ethoxy-4-ethyl-β-carbolin-3-carboxylic acid ethyl ester,
6-ethoxy-4-phenyl-β-carbolin-3-carboxylic acid ethyl ester,
4-methyl-6-methylthio-β-carbolin-3-carboxylic acid methyl ester,
4-ethyl-6-methylthio-β-carbolin-3-carboxylic acid methyl ester,
6-methylthio-4-phenyl-β-carbolin-3-carboxylic acid methyl ester,
6-nitro-β-carbolin-3-carboxylic acid ethyl ester,
4-methyl-6-nitro-β-carbolin-3-carboxylic acid ethyl ester,
4-ethyl-6-nitro-β-carbolin-3-carboxylic acid ethyl ester,
6-nitro-4-propyl-β-carbolin-3-carboxylic acid ethyl ester,
6-nitro-4-phenyl-β-carbolin-3-carboxylic acid ethyl ester,
6-amino-4-methyl-β-carbolin-3-carboxylic acid ethyl ester,
6-amino-4-ethyl-β-carbolin-3-carboxylic acid ethyl ester,
6-amino-4-propyl-β-carbolin-3-carboxylic acid ethyl ester,
6-amino-4-pheny-β-carbolin-3-carboxylic acid ethyl ester,
6-acetamido-4-methyl-β-carbolin-3-carboxylic acid ethyl ester,
6-formamido-4-methyl-β-carbolin-3-carboxylic acid ethyl ester,
6-acetamido-4-ethyl-β-carbolin-3-carboxylic acid ethyl ester,
6-acetamido-4-phenyl-β-carbolin-3-carboxylic acid ethyl ester,
6-methoxy-β-carbolin-3-carboxylic acid dimethylamide,
6-methoxy-β-carbolin-3-carboxylic acid methyl ester,
6-amino-4-methyl-β-carbolin-3-carboxylic acid N-methylamide,
6-amino-4-phenyl-β-carbolin-3-carboxylic acid N-methylamide,
6-acetamido-4-methyl-β-carbolin-3-carboxylic acid N-methylamide,
6-bromo-β-carbolin-3-carboxylic acid N-methylamide,
6-nitro-β-carbolin-3-carboxylic acid N-methylamide,
6-cyano-4-methyl-β-carbolin-3-carboxyic acid ethyl ester,
6-cyano-4-ethyl-β-carbolin-3-carboxylic acid ethyl ester,
6-cyano-4-phenyl-β-carbolin-3-carboxylic acid ethyl ester,
4-methyl-β-carbolin-3,6-dicarboxylic acid dimethyl ester,
4-methyl-β-carbolin-3,6-dicarboxylic acid diethyl ester,
4-ethyl-β-carbolin-3,6-dicarboxylic acid dimethyl ester,
4-phenyl-β-carbolin-3,6-dicarboxylic acid diethyl ester,
4-phenyl-β-carbolin-3,6-dicarboxylic acid dimethyl ester,
6-N,N-dimethylsulphonamido-β-carbolin-3-carboxylic acid ethyl ester,
8-methyl-β-carbolin-3-carboxylic acid N-methylamide,
6,8-dinitro-β-carbolin-3-carboxylic acid N-methylamide,
6,8-dibromo-β-carbolin-3-carboxylic acid ethyl ester hydrobromide,
6,8-dibromo-4-methyl-β-carbolin-3-carboxylic acid ethyl ester,
6,8-dibromo-4-ethyl-β-carbolin-3-carboxylic acid ethyl ester,
6-bromo-8-methyl-β-carbolin-3-carboxylic acid ethyl ester,
6-chloro-8-methyl-β-carbolin-3-carboxylic acid ethyl ester,
6-methoxy-β-carbolin-3-carboxylic acid methyl ester,
8-methyl-6-nitro-β-carbolin-3-carboxylic acid ethyl ester,
6,8-dinitro-β-carbolin-3-carboxylic acid ethyl ester,
8-bromo-6-nitro-β-carbolin-3-carboxylic acid ethyl ester,
7-amino-β-carbolin-3-carboxylic acid ethyl ester dihydrochloride,
6-bromo-7-methoxy-β-carbolin-3-carboxylic acid ethyl ester,
6-iodo-β-carbolin-3-carboxylic acid ethyl ester, and
6-amino-β-carbolin-3-carboxylic acid ethyl ester.

The compounds of this invention may be prepared by one of the following methods, details of which are fully conventional:

(a) by dehydrogenating a compound of Formula II

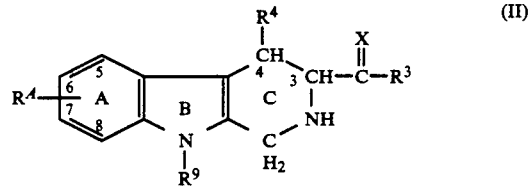

wherein X, $R^3$, $R^4$, $R^A$ and $R^9$ are as defined above, (b) by esterifying a compound of Formula III

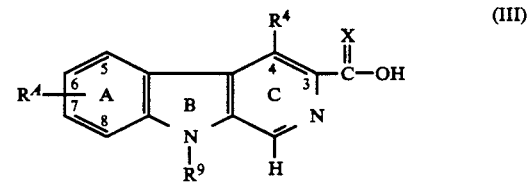

wherein X, $R^4$, $R^A$ and $R^9$ are as defined above, and optionally amidating or reesterifying the ester thus obtained, (c) by reacting a compound of Formula III above, or a functional derivative of said compound, with a compound of Formula IV,

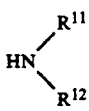

(IV)

wherein $R^{11}$ and $R^{12}$ are as defined above, and optionally reacting the amide thus formed with $P_2S_5$ to form the corresponding thioamide, or, when $R^{11}$ is hydrogen, with thionyl chloride to form a compound of Formula V,

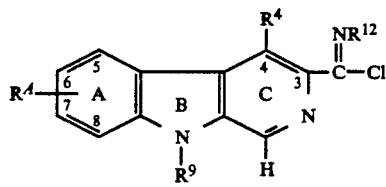

(V)

and reacting the compound thus formed with a compound of the formula $H_2NR^{10}$, wherein $R^{10}$ is as defined above, to form a compound of Formula VI

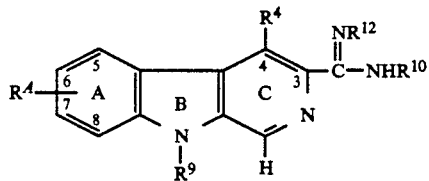

(VI)

(d) by reacting a nitrile of Formula VII

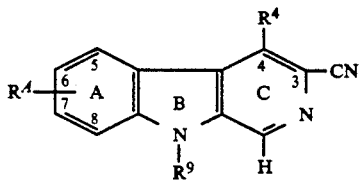

(VII)

wherein $R^4$, $R^A$ and $R^9$ are as defined above with an alcohol and anhydrous hydrogen chloride to form the corresponding imino compound and then reacting this imino compound with a compound of Formula IV above wherein $R^{11}$ and $R^{12}$ are as defined above to form the corresponding amidine, (e) by halogenating a compound of Formula I, wherein X, $R^3$, $R^4$, $R^A$ and $R^9$ are as defined above, and optionally alkoxylating or thioalkylating the halogenated compound thus formed, and (f) by nitrating a compound of Formula I, wherein X, $R^3$, $R^4$, $R^A$ and $R^9$ are as defined above, and optionally reducing the nitrated compound thus formed to form the corresponding amino compound, optionally converting the amino compound via a diazo compound into the corresponding nitrile or halogenated compound, optionally hydrolyzing the nitrile to form the corresponding acid, or optionally acylating the amino compound to form the corresponding amide.

The dehydrogenation of the compound of Formula II (method (a)) can be carried out by several different methods which are well known per se.

One of these methods comprises dissolving or suspending the starting material in an inert solvent. Suitable solvents potentially include all aprotic solvents, the boiling points of which are above 100° C. and which are inert with respect to the starting material. Aromatic solvents are preferred and examples of such solvents include xylene, anisole, toluene, chlorobenzene and diphenyl ether. Elemental sulphur is then added in an amount corresponding to at least one mole equivalent of sulphur per double bond. A slight excess of sulphur is not only harmless but advantageous.

The reaction mixture is boiled at reflux for several hours and the progress of the reaction may be followed by thin layer chromatography.

In a second method the starting material is dehydrogenated with dichloro-dicyano-benzoquinone or chloranil in benzene, xylene, dioxane, tetrahydrofuran, methylene chloride or dimethoxy ethane at temperatures of from 0° to 60° C. for a period of from 0.5 to 4 hours.

In a third method the starting material is dehydrogenated in a boiling solvent, such as xylene, mesitylene and cumene, e.g., at a temperature of from 120° to 180° C. in the presence of a noble metal catalyst, such as platinum in finely divided form, palladium-black and palladium-carbon and with reaction times of from 2 to 16 hours.

The esterification and the optional reesterification (method (b)) is also carried out according to methods which are well known per se.

The esterification is preferably carried out by dissolving or suspending the β-carbolin-3-carboxylic acid and a small excess of triethylamine in tetrahydrofuarn, adding to the reaction mixture an ester of chloroformic acid and by reacting the mixed anhydride thus obtained with the appropriate alcohol.

The reesterification may be carried out (1) with an excess of alcohol in the presence of copper(II) bromide at temperatures above room temperature, (2) under alkaline conditions by using the corresponding alkali metal alcoholate or (3) under acid conditions by introducing hydrogen chloride into the alcohol solution to saturate it at temperatures below room temperature.

The amidation of the ester can also be carried out by methods which are well known per se. The ester, such as an alkyl ester, may be suspended or dissolved in a solvent having a high boiling point, e.g., ethylene glycol or dioxane and an amine is added in excess of the stoichiometric amount. It may be desirable to heat the reaction mixture.

In another method the reaction between the ester and the amine is carried out in the absence of a solvent by heating a mixture of the compounds. If the alcohol thus formed has a lower boiling point than that of the amine, it is removed by evaporation as it is formed.

The ester is preferably reacted with an activated salt of the amine. Such an activated salt may be obtained by reacting the amine with a Grignard reagent, e.g., ethylmagnesiumiodide.

Examples of suitable reactive functional derivatives for use in method (c) are acid chlorides, which can be prepared in various ways, e.g., with thionyl chloride, triphenylphosphine and tetrachloromethane or phosphorhalogenide; anhydrides of the carboxylic acid and a monoester of carbonic acid, e.g., the ethyl ester; and lower alkyl esters of the carboxylic acid.

Method (c) is preferably carried out by dissolving or suspending the β-carbolin-3-carboxylic acid and a small excess of triethylamine in tetrahydrofuran and by adding to the reaction mixture an ester of chloroformic acid. The temperature of the mixture thus formed is preferably maintained at a value of −15° to 40° C. and after some time, usually 1-3 hours, the compound of Formula III is added.

The halogenation of the compounds of Formula I (method (e)) is likewise carried out in accordance with methods known per se. Thus, the starting material may be dissolved in an inert solvent and reacted with the corresponding halogen, such as chlorine or bromine, optionally in the presence of a basic catalyst, at temperatures below room temperature. Inert solvents include, for example, chlorinated hydrocarbons, such as methylene chloride, chloroform, dichloroethylene, etc. Suitable basic catalysts are pyridine and substituted pyridines, such as dimethylaminopyridine. A basic catalyst is unnecessary in chlorination.

The nitration of compounds of Formula I (method (f)) is likewise carried out in accordance with methods known per se. Thus, the starting material may be reacted at temperatures below room temperature with highly concentrated nitric acid or a mixture of concentrated nitric acid and sulfuric acid. The acid used in the nitration operation serves both as reagent and as solvent.

The optional alkoxylation and the thioalkylation of compounds of Formula I (method (e)) is likewise carried out in accordance with methods known per se.

It may be desirable to substitute a bromine substituent with an alkoxy or alkylthio group. Thus, to prepare alkoxy compounds, a bromine compound is heated with the corresponding alkali metal alcoholate, for example, sodium methylate, or potassium ethylate, in the presence of N-methylpyrrolidone under a protective gas to temperatures above 100° C.

To prepare the alkylthio compounds, the bromine compound is reacted in an analogous manner with a freshly prepared lithium alkylmercaptide solution in N-methylpyrrolidone.

The optional reduction of the resulting nitro compound of Formula I (method (f)) to the corresponding amino compounds of Formula I is likewise carried out in accordance with methods known per se.

In a preferred method the reduction is effected with hydrogen in the presence of a metal catalyst, such as Raney nickel, platinum in finely divided form or palladium on a suitable carrier, such as carbon or limestone, at normal pressure and at room temperature. However, it is also possible to use nascent hydrogen, for example, by using a mixture of zinc and hydrochloric acid.

The conversion of the resulting amino compounds of Formula I (method (f)) is likewise carried out in accordance with methods known per se, for example, by a Sandmeyer reaction, in which the diazotization product is directly converted into the corresponding nitrile or halide by reaction with an alkali metal cyanide or alkali halide, respectively, optionally in the presence of the corresponding copper (I) salts, at an elevated temperature.

The nitrile of Formula I can be hydrolyzed, if desired, in a manner known per se, to form the corresponding carboxylic acid. If the nitrile has an ester group in the 3-position, the ester group will also be hydrolyzed and a dicarboxylic acid is obtained.

The hydrolysis is preferably carried out in an alkaline medium in the presence of a higher boiling solvent, such as ethylene glycol, at the boiling temperature of the reaction mixture.

A dicarboxylic acid prepared as described above may be esterified without prior purification. The esterification may be effected in accordance with method (b) described above.

The acylation of the carboxylic acid prepared in accordance with method (f) may be effected with a carboxylic acid anhydride, such as acetic anhydride, e.g., in the presence of an organic base, such as pyridine, and at temperatures about or below room temperature, or with formic acid, optionally in the presence of acetic anhydride, at room temperature or above.

The work-up of the compounds prepared in accordance with methods (a)–(f) described above may be carried out according to generally known methods, e.g., by extraction, crystallization, chromatography, etc.

The starting materials used in methods (a)–(f) can be prepared by methods disclosed in the literature, e.g., Canadian Patent Specification No. 786,351.

A preferred method of preparing said starting materials comprises condensing a substituted or unsubstituted tryptophan or tryptophanester with formaldehyde at elevated temperature to form a tetrahydro-$\beta$-carbolin-3-carboxylic acid ester. The reaction of tryptophanester with formaldehyde is preferably carried out in a non-aqueous medium, e.g., toluene. The water formed is removed by evaporation. The reaction product can be used directly, i.e., without work-up, as a starting material in method (a).

A formyltryptophan ester may be reacted with phosphorous oxychloride or polyphosphoric acid to form a 3,4-dihydro-$\beta$-carbolin-3-carboxylic acid ester, which, however, disproportionates into the corresponding tetrahydro compound and the fully aromatized compound.

The compounds of this invention are pharmacologically active and can be used for the formulation of pharmaceutical preparations, e.g., for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxy-ethoxylated castor oil, gelatine, lactose, amylose, magnesium stearate, talc, silicic acid, fatty acid monoglycerides and diglycerides, pentaerythritol fatty acid esters, hydroxymethylcellulose and polyvinyl pyrrolidone.

The pharmaceutical preparations can be sterilized and mixed, if desired, with such auxiliary agents, e.g., lubricants, preservatives, stabilizers, wetting agents, emulsifiers, salts for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxyethoxylated castor oil.

Ampoules are convenient unit dosages.

For oral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed.

Generally, the compounds of this invention are dispensed in unit dosage form comprising 0.05–10 mg in a pharmaceutically acceptable carrier per unit dosage.

The dosage of the compounds according to this invention is 0.1-300 mg/day, preferably 1-30 mg/day, when administered to patients, e.g., humans, as a drug.

It is well known (Squires, R. F. and Braestrup, C., Nature (London) 266 (1977), 734) that specific sites in the central nervous systems of vertebrates exhibit a high specific affinity for binding 1,4- and 1,5-benzodiazepines. These sites are called benzodiazepine receptors.

The pharmacological properties of the compounds of this invention have been investigated by determining their capability for displacing radioactively labelled flunitrazepam from such benzodiazepine receptors.

The displacement activity of the compounds of the invention has been determined by determining the $IC_{50}$ value and $ED_{50}$ value.

The $IC_{50}$ value represents the concentration which causes a displacement of 50% of the specific binding of $^3H$-flunitrazepam (1.0 nM, 0° C.) in samples comprising a total volume of 0.55 ml of a suspension of brain membrane, e.g., from rats.

The displacement test is performed as follows:

0.50 ml of a suspension of non-treated rat forebrain in 25 mM $KH_2PO_4$, pH=7.1 (5-10 mg tissue/sample) were incubated for 40-60 minutes at 0° C. together with $^3H$-diazepam (specific activity 14.4 Ci/mmol, 1.9 nM) or $^3H$-flunitrazepam (specific activity 87 Ci/mmol, 1.0 nM). After incubation, the suspension was filtered through "Whatman GF/C" glass fiber filters, the residue washed twice with cold buffer solution and the radioactivity measured by scintillation counting.

The test is repeated except that prior to the addition of the radioactively labelled benzodiazepine a given amount or an excessive amount of the compound, the displacement capability of which is to be determined, is added. Based on the data obtained, the $IC_{50}$ value can be calculated.

The $ED_{50}$ value represents the dose (mg/kg) of a test substance which causes the specific binding of flunitrazepam to benzodiazepin receptors in a living brain to be reduced to 50% of the control value. Such an in vivo test is carried out as follows:

Groups of mice are injected with the test substance at different doses and usually subcutaneously. 15 minutes later, $^3H$-flunitrazepam is given intravenously to the mice and after an additional 20 minutes, the mice are killed. Their forebrain membranes are removed and the radioactivity of the forebrain membranes is measured by scintillation counting. The $ED_{50}$ value is determined from dose-response curves.

The data obtained is shown in the following Table V.

The compounds of this invention exhibit antiaggressive effects on mice. The inhibition of aggression has been determined on male mice (NMR from Mollegaard, Denmark) having a weight of 20-22 g. The mice are isolated for 3 weeks in plastic cages and when two mice subsequently are brought into the same cage, they will spontaneously and almost instantaneously start fighting. This aggression is efficiently inhibited by a number of psycho-active drugs including benzodiazepins (Valcelli, Mod. Probl. Pharmacopsych., 1979, 14, 143-156). The compounds of the invention totally inhibited aggression in a test described by Buus Lassen, Europ. J. Pharmacol., 1978, 47, 45-49. The compounds of the invention were administered subcutaneously and orally and the antiagressive effect after ½ hour was determined. Based on the data obtained, the $ED_{50}$ value has been calculated.

Test results obtained by testing some of the compounds of this invention and some well known tranquilizers are also shown in Table V.

The inhibition of motor coordination in mice was also studied 30 minutes after subcutaneous administration in accordance with a method described in the literature (Buus Lassen et al, Acta pharmacol. et toxicol., 1971, 39, 1-16).

Test results obtained by testing some of the compounds of this invention and some well known tranquilizers again are shown in the following Table V.

The acute toxicity in mice was determined by recording the number of deaths within 24 hours.

TABLE V

Test Substance

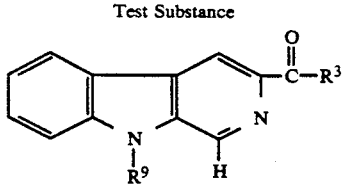

| | | Inhibition of $^3H$ flunitrazepam binding | | Inhibition of agression (h) | Ataxia (Motorincoordination) | Acute Toxicity |
| | | in vitro | in vivo | | | |
| | | $IC_{50}$ | $ED_{50}$ | $ED_{50}$ | $ED_{50}$ | $LD_{50}$ |
| wherein | | ng/ml | mg/kg s.c. | mg/kg s.c. | mg/kg | mg/kg |
| $R^3$ | $R^9$ | | | | | |
| $OC_2H_5$ | H | 1.4 | 60 | 4 | >100 | >500 |
| $OC_5H_{11}$ | H | 12 | >250 | 50 | | |
| $NH(CH_3)$ | H | 100 | 25 | | | |
| $NH(C_2H_5)$ | H | 110 | 42 | 18 | >100 | <250 |
| $NH(iso\text{-}C_3H_7)$ | H | 150 | 23 | 75 | | |
| $NH(CH_2C_6H_5)$ | H | 17 | >250 | | | |
| $NH(C_3H_5)$ | H | 44 | 38 | | | |
| $N\ C_2H_5(C_2H_5)$ | H | 4300 | 82 | 35 | | |
| $N\ CH_3(C_6H_5)$ | H | >4000 | >250 | | | |
| 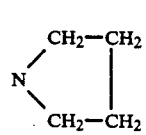 | H | 3300 | >250 | | | |

Test Substance

TABLE V-continued

| R³ | R⁹ | Inhibition of ³H flunitrazepam binding in vitro IC₅₀, ng/ml | Inhibition of ³H flunitrazepam binding in vivo ED₅₀, mg/kg s.c. | Inhibition of aggression (½h) ED₅₀, mg/kg s.c. | Ataxia (Motorincoordination) ED₅₀, mg/kg | Acute Toxicity LD₅₀, mg/kg |
|---|---|---|---|---|---|---|
| N(CH₂—CH₂)₂CH₂ (pyrrolidine-CH₂ ring) | H | 360 | >250 | | | |
| NH(CH₂CH₂OH) | H | 200 | 56 | | | |
| NH(CH₂COOC₂H₅) | H | 160 | >250 | | | |
| NH(CH₂CONH₂) | H | 920 | >250 | | | |
| N(CH₂—CH₂)₂N—CH₃ | H | >4000 | >250 | | | |
| NH(C₂H₅) | COOC₂H₅ | 160 | >100 | | | |
| Chlordiazepoxide ("LIBRIUM" ®)* | | | | 45 | 50 | 700 |
| Diazepam ("STESOLID" ®)* | | | | 3 | 3 | 80 |

*Administered as commercial injection preparations.

It can be seen from Table V that in contrast to the benzodiazepins, chlordiazepoxide and diazepam, the compounds of this invention inhibit aggression without causing impaired motor coordination. In other words, the compounds of this invention do not exhibit the sedative or other unwanted muscle relaxant properties of the benzodiazepins. Therefore, the compounds of this invention are suitable for use as non-sedating anticonvulsants, antiaggressives and anxiolytics or for stress protection. As such, they can be used for treatment of the following illustrative indications: anxiety and tension conditions, with and without depressions, unrest, and disturbances resulting from stress situations or excess of stimulations, as well as pathological aggressiveness.

Inhibition of exploratory motility in rodents is a widely used test for sedative effect. A compound of this invention and two well known tranquilizers have been subjected to such a test.

30 Minutes after subcutaneous administration of physiological saline and test substances, rats were transferred to a novel cage and the motility was measured for the first 10 minutes. The ED₅₀ is the dose inhibiting the motility by 50% as compared to the controls.

The following test results were obtained:

TABLE VI

| Test Substance | ED₅₀, mg/kg |
|---|---|
| Ethyl-β-carbolin-3-carboxylic acid ester | >100 |
| Chlordiazepoxide* ("LIBRIUM" ®) | 1.2 |
| Diazepam* ("STESOLID" ®) | 0.4 |

*Administered as commercial injection preparations.

As shown in Table VI, the ED₅₀-value of the compound of this invention is much higher than that of the well known tranquilizers.

Some of the compounds of this invention have shown an awakening effect in rats without producing the abnormal behaviors produced by the classical abused central stimulants (e.g., amphetamines).

The locomotor activity of rats exhibits a circadian rhythm. Normal locomotion, grooming and eating occur during the dark period and rest during the light period. If CNS stimulants are given to rats which have stayed in their cages for several hours, a pronounced hypermotility is observed during the light period (Buus Lassen, Psychopharmocologia 1973, 29, 55-64; Kallman and Isaac, Psychopharmacologia 1975, 40, 313-318).

Psysiological saline and test substances were administered s.c. or p.o. to rats kept in familiar cages. The motility was measured for 4 hours (2 periods of 2 hours) after administrations. The motility of groups receiving test substances was compared (Student's t-test) with the motility of the saline-treated control group. Physiological saline induced a transient increase of motility consisting of locomotion, sniffing and grooming; about 30 min. after the administration, the motility decreased and the rats spent most of their time resting together in a group. Amphetamine 0.5–5 mg/ig s.c. produced a significant hypermotility consisting of continuous, sterotyped sniffing, rearing and licking on the cage walls. Diazepam 10–20 mg/kg s.c. did not influence motility.

β-Carbolin-3-carboxylic acid ethyl ester, 20–100 mg/kg s.c., and β-carbolin-3-carboxylic acid methylamide 20–100 mg/kg p.o., increased the motility significantly ($P < 0.001$). The rats receiving these compounds appeared more alert than the controls during the experimental period and showed more spells of locomotion, eating and grooming, which is the normal behavioral patterns of rats during the awake state in the dark period. This means that the compounds of this invention have elicited a normal awake behavior during the rest period, whereas amphetamine induced an abnormal behavior which never occurs in saline-treated control rats. These results indicate the usefulness of the compounds of this invention as psychic energizers. As such they may be used to treat indications such as lack of energy, drive and desire as well as lack of concentration and memory.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE A 2.77 g of 6-nitrotryptophanethyl ester is heated to boiling in 30 ml of toluene with 300 mg of paraformaldehyde for 15 hours on a water separator, and then concentrated by evaporation in vacuo. The red-brown residue is finely powdered, suspended in 50 ml of 2N hydrochloric acid and stirred for 15 hours at 60° C. After cooling, the pH is adjusted to 10 with dilute sodium hydroxide solution and the solution is filtered. The filtrate is extracted with ethyl acetate. The filter residue and the ethyl acetate extracts, which have been concentrated by evaporation, are combined and chromatographed on silica gel with methylene chloride-acetone (1:1). 1.6 g of 7-nitro-1,2,3,4-tetrahydro-$\beta$-carbolin-3-carboxylic acid ethyl ester of melting point 255° C. (decomposition) is obtained.

In the same manner the following compounds were prepared:
8-fluoro-1,2,3,4-tetrahydro-$\beta$-carbolin-3-carboxylic acid ethyl ester,
7-chloro-1,2,3,4-tetrahydro-$\beta$-carbolin-3-carboxylic acid ethyl ester,
8-chloro-1,2,3,4-tetrahydro-$\beta$-carbolin-3-carboxylic acid ethyl,
5-nitro-1,2,3,4-tetrahydro-$\beta$-carbolin-3-carboxylic acid ethyl ester,
6-cyano-1,2,3,4-tetra-$\beta$-carbolin-3-carboxylic acid ethyl ester,
5-methyl-1,2,3,4-tetrahydro-$\beta$-carbolin-3-carboxylic acid ethyl ester,
8-methyl-1,2,3,4-tetrahydro-$\beta$-carbolin-3-carboxylic acid ethyl ester,
8-methoxy-1,2,3,4-tetrahydro-$\beta$-carbolin-3-carboxylic acid ethyl ester and
5-chloro-2-hydroxymethyl-6-methoxy-1,2,3,4-tetrahydro-$\beta$-carbolin-3-carboxylic acid ethyl ester.

EXAMPLE B 950 mg of 5-fluorotryptophan is dissolved in 17.5 ml of 0.25N sodium hydroxide solution and 4.6 ml of 40% formalin and stirred at 50° C. until reaction is complete (about 20 hours, thin-layer chromatography check).

The resulting suspension is adjusted to pH 5.5 with 2N hydrochloric acid and, after standing for a while at 0° C., is suction-filtered, washed with water and dried. The crude mixture is dissolved in 30 ml of ethanol and 20 ml of benzene and esterified azeotropically while introducing hydrogen chloride (thin-layer chromatography check). After distilling off the solvent in vacuo, the residue is suspended in water and adjusted at 0° C. to pH 10 with dilute ammonia. After 60 minutes, the solution is suction-filtered and washed well with water. After drying, 797 mg of 6-fluoro-1,2,3,4-tetrahydro-$\beta$-carbolin-3-carboxylic acid ethyl ester of melting point 170°–175° C. remains.

In an analogous manner, 7-fluoro-1,2,3,4-tetrahydro-$\beta$-carbolin-3-carboxylic acid ethyl ester in a yield of 51% is obtained from 6-fluorotryptophan.

EXAMPLE C 1.13 g of 2-(4-chloroindol-3-ylmethyl)-2-aminomalonic acid diethylester hydrochloric and 80 mg of paraformaldehyde are boiled at reflux for about 15 minutes in 30 ml of benzene until the Ninhydrin reaction has disappeared. After cooling, the crystalline precipitate is suction-filtered and recrystallized from benzene. 1.05 g of 5-chloro-1,2,3,4-tetrahydro-$\beta$-carbolin-3,3-dicarboxylic acid ethyl ester hydrochloride of melting point 157° C. is obtained.

700 mg of this diester is hydrolyzed by heating under reflux in 8 ml of 1N sodium hydroxide solution and 8 ml of ethanol. After distilling off the alcohol in vacuo by adjusting the aqueous solution of the dicarboxylic acid to pH 4–4.5 with 1N hydrochloric acid, with simultaneous decarboxylation, 5-chloro-1,2,3,4-tetrahydro-$\beta$-carbolin-3-carboxylic acid is precipitated in crystalline form. The yield is 370 mg of melting point 315°–317° C. (decomposition). By azeotropic esterification in benzene-ethanol in the presence of hydrogen chloride, the hydrochloride of the ethyl ester is obtained in quantitative yield. By treating with dilute ammonia, the free base melting at 296° C. (decomposition) is obtained therefrom.

EXAMPLE D 7.8 g of 4-cyano-N-formyltryptophan ethyl ester is dissolved at 0° C. in 40 ml of phosphorus oxychloride and stirred for 18 hours at room temperature. The solution is then concentrated by evaporation in vacuo, the residue partitioned between water and chloroform and the aqueous phase then extracted. The organic phases are washed with water, dried with calcium sulphate and concentrated by evaporation in vacuo. Chromatography on silica gel with methylene chloride-acetone (1:1) of the residue yields 300 mg of 5-cyano-1,2,3,4-tetrahydro-$\beta$-carbolin-3-carboxylic acid ethyl ester of melting point 248° C. in addition to 500 mg of 5-cyano-$\beta$-carbolin-3-carboxylic acid ethyl ester of melting point 310° C., by disproportionation of the 5-cyano-3,4-dihydro-$\beta$-carbolin-3-carboxylic acid ethyl ester.

EXAMPLE E 12 mmoles of 6-methoxy-N-formyltryptophan ethyl ester is dissolved in 75 ml of chloroform and, with the exclusion of moisture, 13 g of polyphosphoric acid ester in 25 ml of chloroform is added thereto and the whole is stirred for 5 hours at room temperature. After standing overnight, extraction with 100 ml of 1N aqueous sodium hydroxide solution is carried out, the mixture is washed with water, dried, filtered and concentrated. The residue is stirred with 1 g of palladium on carbon (5%) in 160 ml of xylene for 2 hours at 100° C. in a nitrogen current. After cooling, it is suction-filtered. By extracting the residue by boiling with ethanol and filtering off the catalyst, 7-methoxy-$\beta$-carbolin-3-carboxylic acid ethyl ester of melting point 274°–275° C. is obtained in 7% yield.

In an analogous manner, 6-carbethoxy-$\beta$-carbolin-3-carboxylic acid ethyl ester, melting point 290°–292° C. (ethanol/hexane) and 5-methoxy-$\beta$-carbolin-3-carboxylic acid ethyl ester, melting point 273°–275° C. (ethanol/hexane) are prepared.

EXAMPLE 1

A solution of 15.0 g L-tryptophan in 90 ml of 0.6N NaOH and 6.07 ml 40% formalin is heated for 25 hours to 53° C. Subsequently, the suspension obtained by the reaction is titrated to pH 5.5 with 21 ml of 3N HCl and is left to stand in a refrigerator at 4° C. for 18 hours. Subsequently, the precipitate is removed by filtration and washed with 150 ml of cold water. The yield of tetrahydro-β-carbolin-3-carboxylic acid is 14.8 g after drying for 24 hours and the melting point is 295.5° C.

7.5 g of the compound thus obtained plus 700 ml 99.9% of ethanol plus 21 ml of concentrated HCl is refluxed for 24 hours and evaporated to dryness. The yield of tetrahydro-β-carbolin-3-carboxylic acid ethyl ester is 7.25 g.

7 g of this ester is added to 100 ml of tetrachloroethane plus 10 g of chloranil and the mixture is refluxed for 1 hour and 20 minutes. After extraction with two portions of 30 ml of 0.2N HCl, the aqueous phases are titrated to pH 9 with concentrated ammonia and are extracted with two portions of 300 ml of ether. After evaporation, the remainder was distributed between an aqueous phase of pH 4.5 and ethyl acetate.

After evaporation of the ethyl acetate, 1.5 g of β-carbolin-3-carboxylic acid ethyl ester, identified by mass spectrometry based on a molecular weight of 240 is obtained. The melting point is 230°–233° C.

The above described reaction can be illustrated by reaction scheme (VIII).

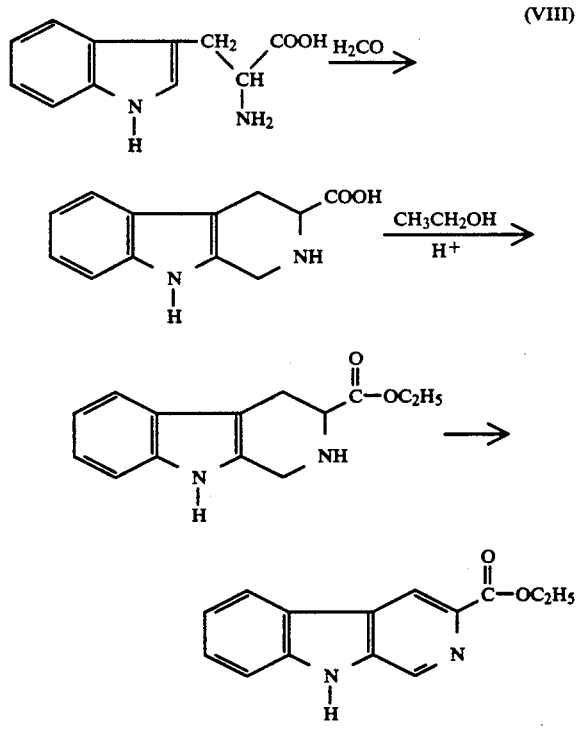

EXAMPLE 2

13 g of polyphosphoric acid, 5 ml of phosphorus oxychloride and 1.0 g D,L-N-formyltryptophan are mixed and are allowed to stand for 2 hours in a warm oil bath at a temperature of 65° C. After cooling, 100 ml ice water is added. After standing, the mixture is filtered and the filtrate is poured onto a column of 25 g "DOWEX" 50 (dry mesh 100–200, 4% cross linked) which previously had been washed with three portions of 50 ml 1M HCl and four portions of 50 ml of distilled water. The column is then washed with two portions of 55 ml of water. The β-carbolin-3-carboxylic acid is then extracted with a mixture of 10 ml of concentrated ammonia and 40 ml of distilled water. The column is washed with a further 20 ml of water. The 70 ml of solution thus obtained is evaporated in a rotary evaporator and produces 0.5 g of red solid. The product is solved in 50 ml of 99% ethanol and is subsequently saturated with hydrogen chloride. Then, the mixture is boiled under reflux for 1 hour and evaporated in vacuo. The remainder is purified by chromatography on silica gel to produce a yield of 105 mg of ethyl β-carbolin-3-carboxylate. Melting point 229° C.

EXAMPLE 3

0.5 g of β-carbolin-3-carboxylic acid, 30 ml of n-pentanol and 5.0 ml of concentrated sulphuric acid are mixed and allowed to stand for 3 hours on a steam bath. After cooling, 30 ml of water and ammonia are added to adjust the pH at about 6. The aqueous phase which was separated from the pentanol phase is washed with 5% sodium bicarbonate solution. The pentanol phase is dried with dry magnesium sulphate and is evaporated. The yield is 0.4 g of n-pentyl β-carbolin-3-carboxylate having a melting point of 209°–212° C. The compound was recrystallized in xylene to produce 0.3 g having a melting point of 216°–219° C.

In an analogous manner, the following compounds of the general formula IX are prepared.

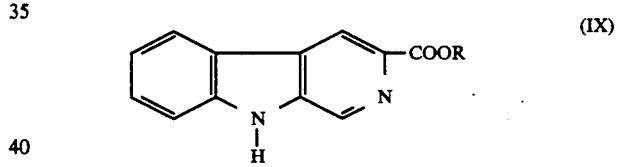

The melting points of these compounds are given in the following Table 1:

TABLE 1

| R | Melting Point, °C. |
|---|---|
| n-C$_3$H$_7$ | 195–197 |
| Iso-C$_3$H$_7$ | 200–202 |
| CH$_2$—CH=CH$_2$ | 191–194 |
| sec C$_4$H$_9$ | 215–217 |
| neo C$_5$H$_{11}$ | 297–300 |
| n-C$_7$H$_{15}$ | 140–141 (HBF$_4$-salt) |
| CH$_2$C$_6$H$_5$ | 234–238 |
| CH$_2$CH$_2$OH | 221–223 |
| CH$_2$CHOH—CH$_2$OH | 114–118 |
| CH$_2$CF$_3$ | 261–264 |

EXAMPLE 4

0.2 g of β-carbolin-3-carboxylic acid, 1 g of phenol and 1 ml of phosphorus oxychloride are mixed in a flask. The homogeneous mixture thus obtained is allowed to stand for two hours on a steam bath. After cooling, 5 ml of ice water are added and the mixture is stirred for 4 hours. The reaction mixture is subsequently neutralized with solid sodium bicarbonate so as to precipitate a light-brown solid. The liquid is removed from the solid by suction and the solid is washed with 1% sodium bicarbonate solution and subsequently with water and finally with ether. The yield is 0.1 g of phenyl β-carbolin-3-carboxylate having a melting point of 237°–239° C. The compound proved to be pure by HPLC and TLC.

In an analogous manner paramethoxyphenyl β-carbolin-3-carboxylate is prepared from β-carbolin-3-carboxylic acid, paramethoxyphenol and phosphorus oxychloride. The melting point of the substance formed is 242°–244° C.

EXAMPLE 5

0.4 g of a 55% suspension of sodium hydride in mineral oil are added to a suspension of 2.1 g of β-carbolin-3-carboxylic acid in 25 ml of dimethyl formamide, and after a period of 5 minutes, 1.2 ml of ethyl chloracetate are added. The mixture is refluxed for 4 hours and subsequently dimethyl formamide is evaporated in vacuo. After addition of 100 ml of water to the remainder, the mixture is extracted with chloroform to form 1 g of carbethoxymethyl β-carbolin-3-carboxylate having a melting point of 202°–203° C.

In an analogous manner 2-N,N-dimethylaminoethyl β-carbolin-3-carboxylate, m.p. 165°–168° C., is prepared.

EXAMPLE 6

A mixture of 2 g of β-carbolin-3-carboxylic acid, 20 ml of thionyl chloride and 2 ml of dimethylformamide is boiled under reflux for 1 hour. The excess thionyl chloride is removed by distillation under reduced pressure. 20 ml of diethylamine is added under cooling to a suspension of the residue in 20 ml of triethylamine and the mixture is concentrated under reduced pressure. The residue is treated with aqueous ammonia (pH 8.5) and the mixture thus obtained is extracted with chloroform (6×25 ml). The extract is washed with water (2×25 ml), dried (K₂CO₃), decolorized with a small amount of charcoal and filtered. The filtrate is evaporated to dryness and the residue is kept at 60° C. overnight. The solid (1.56 g; 62%) is recrystallized from toluene to form β-carbolin-3-carboxylic acid diethylamide having a melting point of 170.0° C.

EXAMPLE 7

A suspension of 5 g of β-carbolin-3-carboxylic acid in a mixture of 900 ml of tetrahydrofuran and 3.6 ml of triethylamine is boiled under reflux for 15 minutes and cooled to room temperature. Freshly distilled ethyl chloroformate (2.5 ml), dissolved in 100 ml of tetrahydrofuran, is added dropwise with stirring over a period of 1¼ hours. After the reaction mixture has been stirred for an additional 30 minutes, a large excess of methylamine is added. Stirring is continued for one hour, whereafter the mixture is filtered and concentrated to approximately 50 ml under reduced pressure. Addition of water (250 ml) causes the amide to precipitate. The mixture is left at 5° C. overnight, filtered and dried at 60° C. for 15 hours. β-carbolin-3-carboxylic acid methylamide thus formed (4.1 g; 77%) is recrystallized from toluene. The melting point is 275° C.

EXAMPLE 8

2 g of ethyl β-carbolin-3-carboxylate and 5 g of β-phenethylamine are heated for 2 hours at 196° C. The cooled, partly crystallized mixture is treated with hot water which is decanted. The residue is recrystallized from xylene to form β-carbolin-3-carboxylic acid (2-phenylethyl)amide (2.5 g) of a melting point of 297°–298° C.

EXAMPLE 9

A solution of 6.0 g of N-methylaniline in 50 ml of ether followed by a solution of 4.0 g of ethyl-β-carbolin-3-carboxylate in 100 ml of tetrahydrofuran is added to ethylmagnesiumiodide, prepared from 1.5 g of magnesium and 9 g of ethyliodide in 75 ml of ether.

The mixture is concentrated to half volume and then refluxed for one hour. After cooling, the reaction mixture is poured into 100 ml of 2N HCl. After addition of potassium carbonate and extraction into chloroform, 3.5 g of N-methyl-N-phenyl-β-carbolin-3-carboxamide (m.p. 237°–240°) is isolated.

EXAMPLE 10

A stirred mixture of 5.0 g of β-carbolin-3-carboxamide dissolved in 100 ml of dry pyridine and 5.0 g of phosphorus pentasulfide is boiled under reflux for 4 hours. The cooled reaction mixture is concentrated to about 25 ml in vacuo and poured into 1 liter of ice water. After adjusting the pH of the mixture to 8.5 with aqueous ammonia, a solid is filtered off, washed thoroughly with water and dried. The substance formed (3.2 g) is recrystallized from n-butyl alcohol to form β-carbolin-3-carbothioamide of a melting point of 274°–276° C.

EXAMPLE 11

Example 7 is repeated except that triethylamine and ethyl chloroformate are used in double amounts, i.e., 7.2 ml and 5.0 ml, respectively. The melting point of 9-carbethoxy β-carbolin-3-carboxylic acid, ethylamide thus prepared is 161°–163° C.

EXAMPLE 12

A mixture of 1.0 g of N'-cyclopropyl-β-carbolin-3-carboxamide and 15 ml of phosphorus oxychloride is boiled under reflux for 1 hour and then evaporated to dryness. The residue is suspended in 25 ml of pyridine previously dried over potassium hydroxide, and about 10 ml of liquid ammonia is added with agitation. After stirring for ½ hour, 100 ml of water is added slowly and the solid is collected. The dry, crude amidine hydrochloride is stirred with conc. aqueous ammonia for 1 hour at 40° C. The solid is collected, air-dried and recrystallized from n-butyl alcohol to form 3-(N-cyclopropylamidino)-β-carbolin having a melting point of 253° C.

The physical properties of some compounds of this invention are summarized in the following Table III:

TABLE III

Physical data

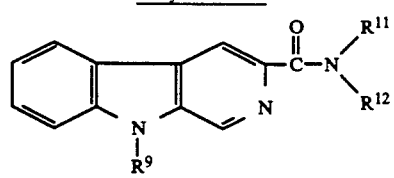

| $R^{11}$ | $R^{12}$ | $R^9$ | Melting Point, °C. |
| --- | --- | --- | --- |
| H | CH₃ | H | 285–287 |
| H | C₂H₅ | H | 248.0–248.5 |
| H | n-C₃H₇ | H | 252–254 |
| H | iso-C₃H₇ | H | 235–237 |
| H | C₆H₅ | H | 304–307 |
| H | CH₂C₆H₅ | H | 276–278 |

TABLE III-continued
Physical data

[Structure: β-carboline with C(=O)-N(R11)(R12) at 3-position, N-R9]

| R11 | R12 | R9 | Melting Point, °C. |
|---|---|---|---|
| H | CH(-CH2-CH2) (cyclopropyl) | H | 248-250 |
| CH3 | CH3 | H | 196-198 |
| C2H5 | C2H5 | H | 169.5-170 |
| CH3 | C6H5 | H | 238-140 |
| | (pyrrolidinyl: CH2-CH2-CH2-CH2) | H | 219-222 |
| | (piperidinyl: CH2-CH2-CH2-CH2-CH2) | H | 220-222 |
| H | OH | H | 237.5-239 |
| H | CH2CH2OH | H | 235-236 |
| H | CH2COOH | H | >320 |
| H | CH2COOC2H5 | H | 207-209 |
| H | CH2CONH2 | H | 314-316 |
| | (piperidinyl with 4-COOCH3) | H | 162-164 |
| | (piperidinyl with 4-CHOH-COOC2H5 / 4-hydroxy-COOC2H5 piperidine) | H | 113-116 |
| | (N-methylpiperazinyl) | H | 201-203 |
| H | C2H5 | COOC2H5 | 161-163 |
| H | n-C4H9 | H | 230-231 |
| H | tert.-C4H9 | H | 263.5-265 |
| H | n-C6H13 | H | 139-141 |
| H | CH2CH2C6H5 | H | 216.5-217.5 |
| H | (CH2)3COOH | H | 277-280 |
| H | D-CH(CHO)-CH(OH)-CH(OH)-CH(OH)-CH2OH | H | >300 |

EXAMPLE 13

10.2 g of 4-methyl-1,2,3,4-tetrahydro-β-carbolin-3-carboxylic acid ethyl ester is dissolved/suspended in 300 ml xylene and the mixture is boiled for 10 minutes in a Dean-Stark apparatus to remove moisture. After cooling to 100°-110° C., 2.1 mole equivalents of sulphur are added and the mixture is boiled under reflux for 5 hours. The progress of the reaction is followed by DC. Subsequently, the xylene is evaporated in vacuo. The remainder is dissolved in chloroform and purified by chromatography (chloroform-ethanol radient) on silica to remove non-reacted sulphur. 4-Methyl-β-carbolin-3-carboxylic acid ethyl ester having a melting point of 235°-239° C. is obtained in a yield of 72%.

EXAMPLE 14

The R-substituted β-carbolin-3-carboxylic acid ethyl esters of the formula I and set forth in the following Table IV are synthesized from the corresponding 4-substituted 1,2,3,4-tetrahydro-β-carbolin-3-carboxylic acid ethyl esters in a manner analogous to the method described in Example 13.

TABLE IV

| R4 | R3 | Yield, % | Melting Point, °C. |
|---|---|---|---|
| C2H5 | OC2H5 | 83 | 174-194 (decomp.) |
| n-C3H7 | " | 56 | 142-160 (decomp.) |
| iso-C3H7 | " | 61 | 190-192 |
| n-C4H9 | " | 50 | 166-169 |
| cyclopentyl | " | 65 | 130 (decomp.) |
| cyclohexyl | " | 72 | 197-201 |
| C6H5 | " | 85 | 237-242 |
| p-CH3O—C6H4 | " | 46 | 180 (decomp.) |
| C5H11 | " | 51 | 172-175 |

EXAMPLE 15

3.1 g of 4-ethyl-1,2,3,4-tetrahydro-β-carbolin-3-carboxylic acid ethyl ester is dissolved in 50 ml of dry toluene and the mixture is cooled to 15° C. and after addition of 5 g of dichlorodicyanobenzoquinone, it is stirred for 1 hour at 15° C. After being diluted with 150 ml of ethyl acetate, the reaction mixture is extracted several times with 5% aqueous ammonia and subsequently washed neutral with saline. After drying with sodium sulphate, filtration and evaporation of the solvent in vacuo, 2.95 g of 4-ethyl-β-carbolin-3-carboxylic acid ethyl ester which is recrystallized from diisopropyl ether is obtained. 2.25 g of the recrystallized compound which is decomposed at 174°-190° C. is obtained.

EXAMPLE 16

6.21 g of 4-methyl-1,2,3,4-tetrahydro-β-carbolin-3-carboxylic acid ester is dissolved in 120 ml of warm mesithylene and after addition of 4.1 g Pd/c (10%), it is boiled under reflux (165° C.) for 7 hours. After cooling, the catalyst is removed by filtration and the catalyst is washed thoroughly with methylene chloride. The combined filtrates are concentrated in vacuo. After recrystallization in acetone, 4.98 g 4-methyl-β-carbolin-3-carboxylic acid ethyl ester having a melting point of 234°-237° C. is obtained.

EXAMPLE 17

Method A 1 g of R4-substituted β-carbolin-3-carboxylic acid ethyl ester is suspended/dissolved in 10 ml of an alcohol and is heated to 50° C. for 5-24 hours after addition of 20 mg of copper (II) bromide. The reaction is followed by TLC. In order to recover the compound formed, ice water is added and the precipitate thus formed is removed by filtration, washed with water, dried and subsequently recrystallized.

Method B 100 mg of sodium is dissolved in 10 ml of an alcohol and subsequently 1 g of an ethyl ester derivative is added. The reaction mixture is heated to 60°-80° C. In order to recover the compound formed, ice water is added and the compound is worked up as described under Method A.

Method C

Hydrogen chloride gas is introduced into a solution or suspension of 1 g of ethyl ester derivative in 10 ml of an alcohol under cooling with ice and until saturation. The reaction mixture is then stirred for 6-24 hours at room temperature. The reaction time is determined by TLC. During work-up, the reaction mixture is admixed with ice/water and the pH value is adjusted at 9-10 by adding concentrated ammonia and under cooling with ice. The precipitated product is further worked-up as described in Method A.

In this manner the following compounds are prepared:
According to Method A:
4-methyl-β-carbolin-carboxylic acid n-propylester, melting point 210°-213° C., and
4-ethyl-β-carbolin-3-carboxylic acid methyl ester, melting point 208°-210° C.
According to Method C:
4-isopropyl-β-carbolin-3-carboxylic acid methyl ester,
4-methyl-β-carbolin-3-carboxylic acid methyl ester, melting point 243°-246° C., and
4-methyl-β-carbolin-3-carboxylic acid 2'-hydroxyethyl ester, melting point 208°-210° C.
And according to Method B:
4-iso-propyl-β-carbolin-3-carboxylic acid 2'-hydroxyethyl ester,
4-iso-propyl-β-carbolin-3-carboxylic acid benzyl ester,
4-ethyl-β-carbolin-3-carboxylic acid n-propyl ester,
4-ethyl-β-carbolin-3-carboxylic acid isopropyl ester,
4-n-propyl-β-carbolin-3-carboxylic acid methyl ester,
4-n-propyl-β-carbolin-3-carboxylic acid n-propyl ester,
4-n-propyl-β-carbolin-3-carboxylic acid 2'-hydroxyethyl ester,
4-iso-propyl-β-carbolin-3-carboxylic acid methyl ester,
4-n-butyl-β-carbolin-3-carboxylic acid methyl ester,
4-n-butyl-β-carbolin-3-carboxylic acid 2'-hydroxyethyl ester
4-n-butyl-β-carbolin-3-carboxylic acid n-propyl ester,
4-cyclohexyl-β-carbolin-3-carboxylic acid methyl ester,
4-cyclohexyl-β-carbolin-3-carboxylic acid propyl ester,
4-phenyl-β-carbolin-3-carboxylic acid methyl ester,
4-phenyl-β-carbolin-3-carboxylic acid n-propyl ester,
4-phenyl-β-carbolin-3-carboxylic acid isopropyl ester,
4-phenyl-β-carbolin-3-carboxylic acid n-butyl ester,
4-phenyl-β-carbolin-3-carboxylic acid 2'-hydroxyethyl ester,
4-n-phentyl-β-carbolin-3-carboxylic acid methyl ester.

EXAMPLE 18

1 g of 4-methyl-β-carbolin-3-carboxylic acid ethyl ester is suspended or dissolved in 20 ml of ethylene glycol. 20-25 Mole equivalents of an amine are added to this mixture and the mixture thus obtained is stirred for 16-24 hours at temperatures ranging from room temperature to 110° C., the time and temperature depending on the reactivity of the amine in question. The reaction is followed by TLC. During work-up, the reaction mixture is poured on ice/water and the precipitate is either removed by filtration or extraction. Excess of high boiling amine which is obtained together with the end product during extraction is removed by high vacuum distillation. After recrystallization, the following compounds are obtained:
4-methyl-β-carbolin-3-carboxamide (yield 95%, melting point 279°-290° C.),
N,4-dimethyl-β-carbolin-3-carboxamide (yield 86.5%, melting point 285°-286° C.),
N,N,4-trimethyl-β-carbolin-3-carboxamide (yield 76.8%, melting point 251°-254° C.),
4-ethyl-β-carbolin-3-carboxamide, N-ethyl-4-ethyl-β-carbolin-3-carboxamide, N-methyl-4-n-propyl-β-carbolin-3-carboxamide, N-methyl-4-iso-propyl-β-carbolin-3-carboxyamide,
N-methyl-4-n-butyl-β-carbolin-3-carboxamide, N-ethyl-4-cyclohexyl-β-carbolin-3-carboxamide, N,N-dimethyl-4-phenyl-β-carbolin-3-carboxamide, N-ethyl-4-phenyl-β-carbolin-3-carboxamide, 4-phenyl-β-carbolin-3-carboxamide and N-methyl-4-phenyl-β-carbolin-3-carboxamide.

EXAMPLE 19

720 mg of 6-fluoro-1,2,3,4-tetrahydro-β-carbolin-3-carboxylic acid ethyl ester and 130 mg of dry sulphur are heated to boiling under nitrogen in 5 ml of xylene. After cessation of dehydrogenation (about 20 hours, thin-layer chromatography check), the solution is concentrated by evaporation in vacuo, and the residue chromatographed on silica gel with chloroform ethanol (95:5). 300 mg of 6-fluoro-β-carbolin-3-carboxylic acid ethyl ester of melting point 284° C. (decomposition) is obtained. After reaction with hydrochloric acid, the hydrochloride which melts at 295° C., with decomposition, is obtained.

EXAMPLE 20

400 mg of 7-nitro-1,2,3,4-tetrahydro-β-carbolin-3-carboxylic acid ethyl ester is dissolved in 40 ml of hot xylene and, after the addition of 400 mg of palladium-carbon (10%), is refluxed for 30 hours. The catalyst is filtered off with suction, and washed out well with warm xylene. The filtrate is concentrated in vacuo, and the residue chromatographed on silica gel with chloroform-ethanol (10:2). 260 mg of 7-nitro-β-carbolin-3-carboxylic acid ethyl ester of melting point 321° C. (decomposition) is obtained.

EXAMPLE 21

2.58 g of 5-methyl-1,2,3,4-tetrahydro-β-carbolin-3-carboxylic acid ethyl ester is dissolved in 40 ml of absolute toluene, cooled to 15° C., 2.72 g of dichlorodicyanobenzoquinone is added thereto and the whole is stirred for 1 hour at this temperature. The mixture is then diluted with ethyl acetate, extracted several times by shaking with dilute ammonia and then with saturated common salt solution, dried over calcium sulphate and concentrated in vacuo. Chromatography on silica gel with a chloroform-ethanol gradient yields 1.56 g of 5-methyl-β-carbolin-3-carboxylic acid ethyl ester of melting point 221°-223° C. (decomposition).

EXAMPLE 22

Analogously to Example 19, from 1,2,3,4-tetrahydro-β-carbolin-3-carboxylic acid esters substituted at the A-ring, the following β-carbolin derivatives of formula 1 are produced:

8-methyl-β-carbolin-3-carboxylic acid ethyl ester, 80% of the theoretical yield, melting point 230°–233° C.;
7-fluoro-β-carbolin-3-carboxylic acid ethyl ester,
6-fluoro-β-carbolin-3-carboxylic acid ethyl ester,
8-fluoro-β-carbolin-3-carboxylic acid ethyl ester,
5-cyano-β-carbolin-3-carboxylic acid ethyl ester, melting point 310° C. (decomposition);
5-chloro-β-carbolin-3-carboxylic acid ethyl ester, melting point 310° C. (decomposition);
7-chloro-β-carbolin-3-carboxylic acid ethyl ester,
8-chloro-β-carbolin-3-carboxylic acid ethyl ester,
7-cyano-β-carbolin-3-carboxylic acid ethyl ester,
5-carbethoxy-β-carbolin-3-carboxylic acid ethyl ester,
5-hydroxymethyl-β-carbolin-3-carboxylic acid ethyl ester,
8-methyl-β-carbolin-3-carboxylic acid ethyl ester, melting point 230°–233° C.;
5-nitro-β-carbolin-3-carboxylic acid ethyl ester,
6-cyano-β-carbolin-3-carboxylic acid ethyl ester,
6-methoxy-β-carbolin-3-carboxylic acid ethyl ester, melting point 235°–238° C.;
6-fluoro-4-methyl-β-carbolin-3-carboxylic acid ethyl ester, melting point 292°–298° C. (decomposition);
5-chloro-6-methoxy-β-carbolin-3-carboxylic acid ethyl ester, melting point 282° C. (ethanol/hexane);
4,6-dimethyl-β-carbolin-3-carboxylic acid ethyl ester, melting point 192°–197° C.;
4-ethyl-6-methyl-β-carbolin-3-carboxylic acid ethyl ester,
6-methyl-4-phenyl-β-carbolin-3-carboxylic acid ethyl ester,
4-ethyl-6-fluoro-β-carbolin-3-carboxylic acid ethyl ester,
6-fluoro-4-propyl-β-carbolin-3-carboxylic acid ethyl ester,
6-fluoro-4-phenyl-β-carbolin-3-carboxylic acid ethyl ester.

EXAMPLE 23

1 g of 6-bromo-β-carbolin-3-carboxylic acid ethyl ester is introduced into 30 ml of ethylene glycol that had been saturated with methylamine, and the mixture is heated for 4 hours with exclusion of moisture at 130°–140° C. After cooling, the mixture is diluted with 70 ml of water, suction-filtered and washed in succession with water, methanol and ether. The filter cake is extracted by boiling in methanol and filtered while hot. After concentration of the filtrate by evaporation, 268 mg of 6-bromo-β-carbolin-3-carboxylic acid-N-methylamide, melting point >310° C., is obtained in 30% yield.

EXAMPLE 24

The following N-methylamides are prepared in accordance with the process described in Example 23:
6-fluoro-β-carbolin-3-carboxylic acid-N-methylamide, yield: 30% of the theoretical yield, mp. 275°–285° C.;
6-methoxy-β-carbolin-3-carboxylic acid-N-methylamide, 55%, mp. 210°–215° C.;
6-nitro-β-carbolin-3-carboxylic acid-N-methylamide, 45%, mp. 280° C. (decomposition);
7-nitro-β-carbolin-3-carboxylic acid-N-methylamide, 20%, mp. >300° C. (decomposition);
8-methyl-β-carbolin-3-carboxylic acid-N-methylamide, 72%, mp. 317°–319° C.; and
6,8-dinitro-β-carbolin-3-carboxylic acid-N-methylamide, 20%, mp. 300° C. (decomposition).

EXAMPLE 25

450 mg of β-carbolin-3-carboxylic acid ethyl ester is slowly added to 4.31 g of bromine and the mixture is stirred for 20 hours at room temperature. After dilution with 30 ml of chloroform, the mixture is filtered with suction and washed with chloroform. The filter cake is heated three times with ethanol and filtered with suction. 411 mg of 6,8-dibromo-β-carbolin-3-carboxylic acid ethyl ester hydrobromide of a melting point >250° C. is thereupon isolated.

EXAMPLE 26

Analogously to Example 25, from the 4-alkyl-β-carbolin-3-carboxylic acid ethyl esters the following compounds are prepared:
6,8-dibromo-4-methyl-β-carbolin-3-carboxylic acid ethyl ester, 45%; and
6,8-dibromo-4-ethyl-β-carbolin-3-carboxylic acid ethyl ester, 62%, mp. 235°–237° C.

EXAMPLE 27

0.5 g of 4-methyl-β-carbolin-3-carboxylic acid ethyl ester (melting point 235°–239° C.) is dissolved in 25 ml of chloroform and 1.7 ml of pyridine and a solution of 1 ml of bromine in 21 ml of chloroform is added dropwise thereto at 0° C. After standing for one hour while cooling with ice and after dilution with 50 ml of methylene chloride, the mixture is extracted by washing with sodium thiosulphate solution, dilute aqueous ammonia solution and water. After drying with sodium sulphate, filtering off and distilling off the solvent in vacuo, 6-bromo-4-methyl-β-carbolin-3-carboxylic acid ethyl ester is obtained in 38% yield, Melting point 231°–232° C. (from acetone).

EXAMPLE 28

Analogously to Example 27, 6-bromo-8-methyl-β-carbolin-3-carboxylic acid ethyl ester of melting point 301°–304° C. (from ethanol) is produced in 87% yield from 8-methyl-carbolin-3-carboxylic acid ethyl ester.

EXAMPLE 29

Analogously to Example 28, from corresponding β-carbolin-3-carboxylic acid ethyl esters, the following are prepared:
6-bromo-β-carbolin-3-carboxylic acid ethyl ester, 47%, melting point 315° C. (pyridine);
6-bromo-4-ethyl-β-carbolin-3-carboxylic acid ethyl ester, mp. 255°–257° C.;
6-bromo-4-phenyl-β-carbolin-3-carboxylic acid ethyl ester, and
6-bromo-7-methoxy-β-carbolin-3-carboxylic acid ethyl ester, mp. 265°–268° C.

EXAMPLE 30

Analogously to Example 27, from 4-alkyl-β-carbolin-3-carboxylic acid methyl esters, the following compounds are prepared:
6-bromo-4-methyl-β-carbolin-3-carboxylic acid methyl ester, mp. 247°–249° C. (methanol); and 6-bromo-4-phenyl-β-carbolin-3-carboxylic acid methyl ester.

EXAMPLE 31

Analogously to Example 27, 6-bromo-4-methyl-β-carbolin-3-carboxylic acid n-propyl ester is prepared from 4-alkyl-β-carbolin-3-carboxylic acid n-propyl ester.

EXAMPLE 32

1 g of 4-methyl-β-carbolin-3-carboxylic acid ethyl ester is dissolved in 120 ml of chloroform saturated at 0° C. with chlorine gas and stirred for 3 hours while cooling with ice. The excess chlorine and part of the chloroform are then distilled with suction in vacuo, the crystalline precipitate is filtered off, suspended in 50 ml of ethyl acetate, and aqueous ammonia (5%, 10 ml) is added thereto. After 10 minutes, the crystalline product had dissolved. After separating off the aqueous phase and washing the organic phase with water, the residue is dried with sodium sulphate, filtered, and the solvent is distilled off in vacuo. The residue is crystallized from ethyl acetate. 0.73 g of 6-chloro-4-methyl-β-carbolin-3-carboxylic acid ethyl ester of melting point 225°–228° C. is obtained.

EXAMPLE 33

Analogously to Example 32, the following compounds are prepared from corresponding β-carbolin-3-carboxylic acid ethyl esters:
6-chloro-β-carbolin-3-carboxylic acid ethyl ester, 61%, melting point 270° C. (pyridine);
6-chloro-4-ethyl-β-carbolin-3-carboxylic acid ethyl ester,
6-chloro-8-methyl-β-carbolin-3-carboxylic acid ethyl ester, 80%, melting point 300°–303° C. (methylene chloride/ethyl acetate); and
6-chloro-4-phenyl-β-carbolin-3-carboxylic acid ethyl ester.

EXAMPLE 34

Analogously to Example 32, from the 4-alkyl-β-carbolin-3-carboxylic acid methyl esters, the following compounds are prepared:
6-chloro-4-methyl-β-carbolin-3-carboxylic acid methyl ester; and
6-chloro-4-phenyl-β-carbolin-3-carboxylic acid methyl ester.

EXAMPLE 35

Analogously to Example 32, 6-chloro-4-phenyl-β-carbolin-3-carboxylic acid n-propyl ester is prepared from 4-phenyl-β-carbolin-3-carboxylic acid n-propyl ester, and 6-chloro-4-methyl-β-carbolin-3-carboxylic acid i-propyl ester is prepared from 4-methyl-β-carbolin-3-carboxylic acid isopropyl ester.

EXAMPLE 36

A solution of 0.6 g of 6-bromo-4-methyl-β-carbolin-3-carboxylic acid ethyl ester, 2.8 g of freshly prepared sodium methylate and 2 g of copper (I) iodide in 20 ml of N-methylpyrrolidone is heated under argon protecting gas for 16 hours at 150°–155° C. After cooling, the mixture is stirred into 100 ml of ice-cold, semi-saturated sodium dihydrogen phosphate solution; and the precipitated product is filtered off, washed with water and dried. After purification by chromatography on silica gel, 0.36 g of 6-methoxy-4-methyl-β-carbolin-3-carboxylic acid methyl ester of melting point 216°–220° C. (diisopropyl ether) is obtained.

EXAMPLE 37

Analogously to Example 36, 6-methoxy-4-methyl-β-carbolin-3-carboxylic acid methyl ester, 4-ethyl-6-methoxy-β-carbolin-3-carboxylic acid methyl ester and 6-methoxy-4-phenyl-β-carbolin-3-carboxylic acid methyl ester are prepared from the 4-substituted 6-bromo-β-carbolin-3-carboxylic acid methyl esters.

EXAMPLE 38

By alkaline transesterification, the corresponding ethyl, propyl and isopropyl esters are prepared from the 3-carboxylic acid methyl esters. The following compounds are obtained:
6-methoxy-4-methyl-β-carbolin-3-carboxylic acid ethyl ester,
4-ethyl-6-methoxy-β-carbolin-3-carboxylic acid n-propyl ester, and
6-methoxy-4-phenyl-β-carbolin-3-carboxylic acid ethyl ester.

EXAMPLE 39

Analogously to Example 36, the following compounds are prepared from 6-bromo-4-alkyl-β-carbolin-3-carboxylic acid ethyl esters:
6-ethoxy-4-methyl-β-carbolin-3-carboxylic acid ethyl ester,
6-ethoxy-4-ethyl-β-carbolin-3-carboxylic acid ethyl ester, and
6-ethoxy-4-phenyl-β-carbolin-3-carboxylic acid ethyl ester.

EXAMPLE 40

At $-10°$ C. methylmercaptan is introduced into 150 ml of tetrahydrofuran. Within 2 hours, at $-10°$ C., 100 ml of 1.6 molar butyl lithium solution (hexane) is added dropwise thereto. The whole is then stirred for 30 minutes and the solvent is then distilled off in vacuo at a bath temperature of 20° C. The lithium methylmercaptide thus prepared is dissolved in 100 ml of N-methylpyrrolidone. 10.2 g of 6-bromo-4-methyl-β-carbolin-3-carboxylic acid ethyl ester is added thereto, and the whole is heated for 24 hours under argon protecting gas for 24 hours at 100° C. For work-up, the mixture is stirred into 400 ml of ice water, extracted with ethyl acetate, and the extracts are washed with water until neutral. The crude product obtained in this manner is dissolved in 250 ml of methanol and after the addition of 1 g of sodium methylate, is boiled for 6 hours. The solvent is then distilled off in vacuo, 150 ml of saturated sodium hydrogen phosphate solution is added to the residue and extraction with ethyl acetate is carried out. After washing with water until neutral, drying with sodium sulphate, filtering and distilling off the solvent, 8.85 g of 4-methyl-6-methylthio-β-carbolin-3-carboxylic acid methyl ester is obtained, which is crystallized from diisopropyl ether. Melting point 186°–193° C. (decomposition).

EXAMPLE 41

Analogously to Example 38, 4-ethyl-6-methylthio-β-carbolin-3-carboxylic acid methyl ester and 6-methylthio-4-phenyl-β-carbolin-3-carboxylic acid methyl ester are prepared.

EXAMPLE 42

1 g of β-carbolin-3-carboxylic acid ethyl ester is slowly introduced at room temperature into 20 ml of concentrated nitric acid (65%). After addition is complete, the solution is heated to 70°–75° C., whereupon a clear solution forms. After about 30 minutes, the solution becomes turbid. After a total stirring time of 1.5 hours at 70°–75° C., the solution is allowed to cool and the sediment is poured onto 100 g of ice. After filtering with suction, recrystallization from pyridine is carried out. 6-nitro-β-carbolin-3-carboxylic acid ethyl ester of melting point 320°–325° C. is isolated in 55% yield.

EXAMPLE 43

Analogously to Example 42, at room temperature, 8-methyl-6-nitro-β-carbolin-3-carboxylic acid ethyl ester of melting point 296° C. (decomposition) is obtained in 72% yield from 8-methyl-β-carbolin-3-carboxylic acid ethyl ester.

EXAMPLE 44

5.5 g of β-carbolin-3-carboxylic acid ethyl ester is introduced into a mixture of 30 ml of 100% nitric acid and 0.3 ml of concentrated sulphuric acid in the course of 15 minutes at 5° C., while stirring. After one hour, the clear solution is poured onto plenty of ice and the precipitated substance is filtered with suction. The filter residue is recrystallized from hot dimethyl-sulphoxide and the crystallizate is washed with alcohol and then with diethyl ether. 3.7 g of 6,8-dinitro-β-carbolin-3-carboxylic acid ethyl ester of melting point 341°–345° C. (decomposition) is obtained.

EXAMPLE 45

285 mg of 6-nitro-β-carbolin-3-carboxylic acid ethyl ester is introduced into 5.8 g of bromine and stirred for 2 days at room temperature. The mixture is then diluted with 15 ml of chloroform and filtered with suction. The residue is recrystallized from pyridine and chromatographed on silica gel with chloroform-methanol (9:1). 65 mg of 8-bromo-6-nitro-β-carbolin-3-carboxylic acid ethyl ester of melting point 291°–292° C. is obtained.

EXAMPLE 46

3.2 g of 4-methyl-β-carbolin-3-carboxylic acid methyl ester are added over the course of 10 minutes to an ice-cooled mixture of 10 ml of concentrated nitric acid and 5 ml of fuming nitric acid. After 2 hours' cooling with ice, the reaction solution is stirred into 150 ml of ice water, rendered alkaline (pH 10–11) with concentrated ammonia solution while cooling with ice, extracted with ethyl acetate, washed until neutral with water, dried using sodium sulphate and filtered. The solvent is distilled off in vacuo. The crude product (3.42 g) is crystallized from acetone. 2.28 g of 4-methyl-6-nitro-β-carbolin-3-carboxylic acid ethyl ester of melting point 272°–275° C. is obtained.

EXAMPLE 47

Analogously to Example 46, the following compounds are prepared from corresponding 4-substituted β-carbolin-3-carboxylic acid ethyl esters:
4-ethyl-6-nitro-β-carbolin-3-carboxylic acid ethyl ester, melting point 274°–282° C. (decomposition);
6-nitro-4-propyl-β-carbolin-3-carboxylic acid ethyl ester; and
6-nitro-4-phenyl-β-carbolin-3-carboxylic acid ethyl ester.

EXAMPLE 48

0.1 g of 7-nitro-β-carbolin-3-carboxylic acid ethyl ester is suspended in 30 ml of ethanol and, after the addition of 1 ml of 5N hydrochloric acid, is hydrogenated at normal pressure over 25 mg of platinum dioxide until the theoretical amount of hydrogen has been absorbed. The catalyst is filtered off and washed well with warm ethanol. The filtrate is treated with active carbon and concentrated until turbidity commences. After cooling, 95 mg of 7-amino-β-carbolin-3-carboxylic acid ethyl ester dihydrochloride of melting point 270° C. (decomposition) is obtained.

EXAMPLE 49

1.02 g of 4-methyl-6-nitro-β-carbolin-3-carboxylic acid ethyl ester is dissolved or suspended in 30 ml of ethanol and 6 ml of tetrahydrofuran and, after the addition of 150 ml of palladium-carbon (10%), is hydrogenated at 24° C. and normal pressure. Within 3.5 hours, 210 ml of hydrogen is absorbed. The solution is filtered off and the catalyst and the solvent is distilled off in vacuo. The crude product is recrystallized from methanol-chloroform. 816 mg of 6-amino-4-methyl-β-carbolin-3-carboxylic acid ethyl ester of melting point 225°–238° C. (decomposition) is obtained.

EXAMPLE 50

Analogously to Example 49, the following 6-amino compounds are prepared from the corresponding 6-nitro-β-carbolin-4-carboxylic acid ethyl esters:
6-amino-4-ethyl-β-carbolin-3-carboxylic acid ethyl ester,
6-amino-4-propyl-β-carbolin-3-carboxylic acid ethyl ester,
6-amino-4-phenyl-β-carbolin-3-carboxylic acid ethyl ester, and
6-amino-β-carbolin-3-carboxylic acid ethyl ester, mp. 224°–227° C.

EXAMPLE 51

0.6 g of 6-amino-4-methyl-β-carbolin-3-carboxylic acid ethyl ester is dissolved in 6 ml of pyridine and 1.5 ml of acetic anhydride and the whole is stirred for 16 hours at room temperature. The mixture is then stirred into 30 ml of ice water and intensely extracted with ethyl acetate. The extracts are washed until neutral with semisaturated common salt solution, dried using sodium sulphate and filtered. The solvent is distilled off in vacuo. The residue (0.78 g) is recrystallized from acetone-diisopropyl ether. 0.49 g of 6-acetamido-4-methyl-β-carbolin-3-carboxylic acid ethyl ester of melting point 273°–278° C. is obtained.

EXAMPLE 52

Analogously to Example 51, 6-formamido-4-methyl-β-carbolin-3-carboxylic acid ethyl ester is prepared from 0.45 g of the corresponding 6-amino compound in 5 ml of pyridine with 1 ml of formic acid and 2 ml of acetic anhydride at 0° C. Yield: 0.24 g; melting point 210°–216° C., ethyl acetate.

EXAMPLE 53

Analogously to Example 51, the following 6-acetamido compounds are prepared from the corresponding 6-amino derivatives:

6-acetamido-4-ethyl-β-carbolin-3-carboxylic acid ethyl ester, and 6-acetamido-4-phenyl-β-carbolin-3-carboxylic acid ethyl ester.

EXAMPLE 54

4 ml of dimethylformamide, 250 mg of copper (I) iodide and 160 mg of 6-bromo-β-carbolin-3-carboxylic acid ethyl ester are added to a solution, prepared under argon, of 230 mg of sodium in 3 ml of absolute methanol, and the whole is heated for 6 hours at 145° C. The solution is then concentrated in vacuo, the residue is washed with water, dried and chromatographed on silica gel with chloroform-methanol (8:2). 67 mg of 6-methoxy-β-carbolin-3-carboxylic acid dimethylamide of melting point 195° C. (decomposition) is obtained.

EXAMPLE 55

1.81 g of 6-amino-4-methyl-β-carbolin-3-carboxylic acid ethyl ester is suspended in 15 ml of ethylene glycol and, while cooling with ice, methylamine is introduced until saturation point is reached. The mixture is then stirred at room temperature for 16 hours, stirred into 100 ml of ice water and the product is filtered off, dried and recrystallized from ethanol-chloroform. 1.42 g of 6-amino-4-methyl-β-carbolin-3-carboxylic acid N-methylamide of melting point 281°-285° C. is obtained.

EXAMPLE 56

Analogously to Example 55, the following N-methylamides are prepared from the corresponding 4-substituted 6-amino-β-carbolin-3-carboxylic acid ethyl esters:

6-amino-4-phenyl-β-carbolin-3-carboxylic acid N-methylamide, and 6-acetamido-4-methyl-β-carbolin-3-carboxylic acid N-methyl amide.

EXAMPLE 57

0.3 g of 6-amino-4-methyl-β-carbolin-3-carboxylic acid ethyl ester is suspended in 5 ml of ethylene glycol and, after the addition of 3 ml of dimethylamine, the whole is heated for 22 hours at 100° C. After cooling, the mixture is poured into 30 ml of ice water, extracted with ethyl acetate, washed with water until neutral, dried using sodium sulphate, filtered and the solvent is distilled off in vacuo. The crude product precipitates as a fine brown powder. 0.2 g of 6-amino-4-methyl-β-carbolin-3-carboxylic acid N,N-dimethylamide of melting point 235°-245° C. (decomposition) is obtained.

EXAMPLE 58

Analogously to Example 51, 6-acetamido-4-methyl-β-carbolin-3-carboxylic acid N-methylamide is prepared from 6-amino-4-methyl-β-carbolin-3-carboxylic acid N-methylamide with acetic anhydride.

EXAMPLE 59

12 g of β-carbolin-3-carboxylic acid methyl ester is suspended in 130 ml of methanol; 130 ml of 40% aqueous methylamine is added thereto and the whole is boiled at reflux for 2 hours. After cooling, the mixture is suction-filtered. By extraction with 300 ml of hot methanol and crystallization from dimethylformamide/hexane, the β-carbolin-3-carboxylic acid N-methylamide of melting point 264°-266° C. is isolated from the filter residue in 43% yield.

EXAMPLE 60

1 g of 6-bromo-β-carbolin-3-carboxylic acid ethyl ester is introduced into 30 ml of ethylene glycol that had been saturated with methylamine, and the whole is heated for 4 hours with the exclusion of moisture at 130°-140° C. After cooling, the mixture is diluted with 70 ml of water, suction-filtered and washed in succession with water, methanol and ether. The filter cake is extracted by boiling in methanol and filtered hot. After concentration by evaporation of the filtrate, 268 mg of 6-bromo-β-carbolin-3-carboxylic acid N-methylamide of melting point >310° C. is obtained.

EXAMPLE 61

Analogously to Example 59, β-carbolin-3-carboxylic acid N-ethylamide of melting point 244°-246° C. (from ethanol/hexane) is obtained in 42% yield from 0.2 g of β-carbolin-3-carboxylic acid methyl ester with ethylamine.

EXAMPLE 62

5 ml of 2 molar aqueous sodium nitrite solution is added dropwise, while cooling intensively with ice, to a suspension of 2.7 g of 6-amino-4-methyl-β-carbolin-3-carboxylic acid ethyl ester in 15 ml of 3N sulphuric acid. After 20 minutes, the diazotizing solution is quickly added dropwise to a solution at 60° C. of 1.2 g of copper (I) cyanide in 8 ml of 4.5 molar sodium cyanide solution. After heating for 30 minutes at 60° C., the solution is allowed to stand at room temperature for 2 hours and is then suction-filtered. The filter residue is extracted by boiling with methanol. The combined filtrates are concentrated by evaporation and chromatographed on silica gel with chloroform/ethanol (95:5). 6-Cyano-4-methyl-β-carbolin-3-carboxylic acid ethyl ester of melting point 268°-276° C. (decomposition) is obtained in 25% yield.

EXAMPLE 63

Analogously to Example 62, the following 6-cyano compounds are obtained from the corresponding 6-amino-β-carbolin-3-carboxylic acid ethyl esters:

6-cyano-4-ethyl-β-carbolin-3-carboxylic acid ethyl ester, 6-cyano-4-phenyl-β-carbolin-3-carboxylic acid ethyl ester, and 6-cyano-β-carbolin-3-carboxylic acid ethyl ester.

EXAMPLE 64

2.81 g of 6-cyano-4-methyl-β-carbolin-3-carboxylic acid ethyl ester is heated with 4.6 g of potassium hydroxide in 20 ml of ethylene glycol for 16 hours at 150° C. After cooling to 0° C., 10 ml of acetic acid is added dropwise. The mixture is diluted with 100 ml of water and, after saturation with sodium chloride, is extracted with ethyl acetate. The extracts are washed until neutral with saturated common salt solution, dried using sodium sulphate, filtered, and the solvent is distilled off in vacuo. The crude product is dissolved in 30 ml of 10% methanolic hydrochloric acid and boiled for 5 hours under reflux. After distilling off the solvent in vacuo, 20 ml of dilute aqueous ammonia are added and the mixture is extracted with ethyl acetate. After washing until neutral, drying and distilling off the solvent, the crude product is recrystallized from diisopropyl ether. 1.36 g of 4-methyl-β-carbolin-3,6-dicarboxylic acid dimethyl ester of melting point 199°-204° C. is obtained.

EXAMPLE 65

Analogously to Example 64, the following compounds are prepared from the corresponding 6-cyano-β-carbolin-3-carboxylic acid ethyl esters:
4-methyl-β-carbolin-3,6-dicarboxylic acid diethyl ester,
4-ethyl-β-carbolin-3,6-dicarboxylic acid dimethyl ester,
4-phenyl-β-carbolin-3,6-dicarboxylic acid diethyl ester, and
4-phenyl-β-carbolin-3,6-dicarboxylic acid dimethyl ester.

EXAMPLE 66

1.3 mmoles of 6-amino-β-carbolin-3-carboxylic acid ethyl ester are diazotized at 0° C. in 4 ml of semi-concentrated hydrochloric acid with 1.3 mmoles of sodium nitrite in 2 ml of water. 1.35 mmoles of potassium iodide in 2 ml of water are added to this mixture. The mixture is then slowly heated to 100° C. until the nitrogen evolution has ceased. The mixture is then diluted with 100 ml of water, approximately 20 mg of sodium thiosulphate are added and the mixture is filtered with suction. The residue is extracted by boiling with methylene chloride/acetone, filtered, and the filtrate is concentrated by evaporation. The residue is chromatographed on silica gel with chloroform/ethanol (9:1). 6-Iodo-β-carbolin-3-carboxylic acid ethyl ester of melting point 286°–287° C. (decomposition) is thereupon obtained in 30% yield.

EXAMPLE 67

1 mmole of 6-amino-β-carbolin-3-carboxylic acid ethyl ester is diazotized at 0° C. in 2 ml of 24% aqueous hydrobromic acid with 1 mmole of sodium nitrite in 1 ml of water. This mixture is added dropwise to a solution of 40 mg of copper (I) bromide in 1 ml of 48% aqueous hydrobromic acid at room temperature. After addition is complete, the mixture is heated to 80° C. The temperature is increased to 100° C. until nitrogen evolution has ceased. 10 ml of water is then added and filtration with suction is carried out. The residue is stirred with ammonia and filtered with suction. It is then extracted by boiling with ethanol and concentrated by evaporation. By chromatography on silica gel with an eluant comprising 9 parts of chloroform and 1 part of ethanol, 6-bromo-β-carbolin-3-carboxylic acid ethyl ester of melting point 308°–313° C. is obtained in 35% yield.

EXAMPLE 68

1 g of β-carbolin-3-carboxylic acid ethyl ester is carefully introduced while stirring at 0° C. into 1.5 ml of chlorosulphonic acid. The mixture is then stirred for 30 minutes at room temperature and introduced into plenty of ice water and filtered with suction after standing for a while. The filter residue is added to 2 ml of 40% aqueous dimethylamine solution and stirred for 18 hours. The crystalline precipitate is filtered with suction, washed well with water and chromatographed on silica gel with toluene-glacial acetic acid-water (10:10:1). 200 mg of 6-N,N-dimethylsulphonamido-β-carbolin-3-carboxylic acid ethyl ester is obtained as monohydrate acetate of melting point 272° C. (decomposition).

Analogously the following compounds are prepared:
6-sulfamoyl-β-carbolin-3-carboxylic acid ethyl ester, mp. 320°–324° C.;
6-N-methylsulfamoyl-β-carbolin-3-carboxylic acid ethyl ester, mp. 305°–308° C.;
6-N-methylsulfamoyl-β-carbolin-3-carboxylic acid-N-methylamide, mp. 236°–240° C.;
6-morpholinosulfonyl-β-carbolin-3-carboxylic acid ethyl ester, mp. 309°–312° C.;
6-sulfamoyl-4-methyl-β-carbolin-3-carboxylic acid ethyl ester, mp. 297°–300° C.;
6-N-methylsulfamoyl-4-methyl-β-carbolin-3-carboxylic acid ethyl ester, mp. 239°–244° C.;
6-N,N-dimethylsulfamoyl-4-methyl-β-carbolin-3-carboxylic acid ethyl ester, mp. 253°–256° C.;
6-N,N-diethylsulfamoyl-4-methyl-β-carbolin-3-carboxylic acid ethyl ester, mp. 272°–274° C.; and
6-(4-methylpiperazinosulfamoyl)-4-methyl-β-carbolin-3-carboxylic ethyl ester, mp. 247°–251° C.

EXAMPLE 69

10.0 mg of β-carbolin-3-carboxylic acid monomethylamide is micronized (finely ground) and homogeneously mixed with:
80.0 mg lactose [DAB (German Pharmacopoeia 7); USP XVII],
29.6 mg microcrystalline cellulose, and
0.4 mg magnesium stearate (USP XVII),
and compressed into tablets without previous granulation, these tablets having a weight of 120 mg, with a diameter of about 7 mm and a thickness of 2.7–2.9 mm.

EXAMPLE 70

50.0 mg of β-carbolin-3-carboxylic acid monomethyl amide (micronized, particle size 2–8 μm) is mixed homogeneously with 150 mg of lactose (USP XVII) and filled into hard-gelatin capsules (6×16).

EXAMPLE 71

10 g of finely ground 4-methyl-β-carbolin-3-carbonic acid ethyl ester is dissolved in 200 g of polyhydroxyethoxylated castor oil at 50° C. and the solution is completed to one liter with a 0.25% aqueous solution of sodium chloride. The solution is filtered by a membrane filter to an aseptic condition and filled into ampoules for intravenous administration.

EXAMPLE 72

2.5 g of 5-cyano-β-carbolin-3-carbonic acid ethyl ester is dissolved in 200 g of polyoxyethylene-sorbitan-monooleate at 60° C., completed to one liter with 0.25% solution of sodium chloride in water, filtered and filled into ampoules under aseptic conditions.

EXAMPLE 73

A suspension of 2.5 g of β-carbolin-3-carboxylic acid in a mixture of 450 ml of dry tetrahydrofuran and 1.8 ml of triethylamine is boiled under reflux for 15 minutes and cooled to room temperature. Freshly distilled ethyl chloroformate (1.25 ml) dissolved in 50 ml of dry tetrahydrofuran is added dropwise with stirring over a period of 1 hour. The reaction mixture (1) is stirred for additionally 30 minutes. A solution of 1.9 g of 3,4-dichlorophenol in 25 ml of dry tetrahydrofuran is added to 0.5 g of a 55% sodium hydride dispersion in oil suspended in 75 ml of dry tetrahydrofuran. The solution of the phenolate is added to mixture (1). Stirring is continued for one hour, whereafter the reaction mixture is filtered and concentrated to approximately 50 ml in vacuo. Addition of water (250 ml) causes the ester to precipitate. The mixture is left at 5° C. overnight and filtered. The dry product (3.0 g; 71%) is recrystallized from xylene to give pure β-carbolin-3-carboxylic acid 3,4-dichlorophenyl ester which melts at 260°–261° C.

In an analogous manner β-carbolin-3-carboxylic acid 4-chlorophenyl ester is prepared. M.p. 258°–260° C.

EXAMPLE 74

Analogously to Example 7, but using a solution of 4.2 g of 1.1- or 1.2-dimethylhydrazine in 600 ml of tetrahydrofuran instead of methylamine the following two compounds were prepared: N',N'-dimethyl-β-carbolin-3-carbohydrazide which melts at 209°–212° C. when recrystallized from xylene and N,N'-dimethyl-β-carbolin-3-carbohydrazide, respectively which melts at 272°–278° C.

EXAMPLE 75

A suspension of 10 g of β-carbolin-3-carboxylic acid amide in 250 ml of phosphorus oxychloride is stirred at room temperature until all the amide has dissolved. The solution is then boiled under reflux for 4 hours and the excess of phosphorus oxychloride is evaporated in vacuo. Ice and water are added to the residue to a volume of approximately 1 liter and concentrated ammonia is added until the pH is 8.5. The precipitate is then filtered and washed with water. After drying the yield of β-carbolin-3-carbonitril is 9.1 g; after recrystallization from xylene, the m.p. is 294°–300° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A β-carboline-3-carboxylic acid derivative of the formula

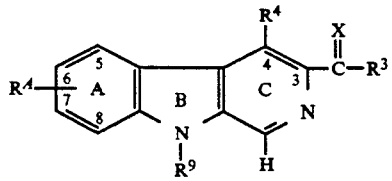

wherein:
X is oxygen, sulphur or $NR^{10}$, wherein $R^{10}$ is hydrogen or alkyl;
$R^3$ is $NR^{11}R^{12}$, wherein $R^{11}$ and $R^{12}$ are the same or different and each is (i) hydrogen, (ii) hydroxy, (iii) $C_{1-10}$-alkyl, (iv) $C_{3-7}$-cycloalkyl, or each of groups (iii)–(iv) optionally substituted with hydroxy, carboxamido, or carboxy, or (v) amino optionally substituted with $C_{1-10}$-alkyl, or wherein $R^{11}$ and $R^{12}$ together with the connecting nitrogen atom form pyrrolidine, piperidine, 3-methoxycarbonyl-piperidine, 4-hydroxy-3-ethoxycarbonylpiperidine, or N-methyl-piperazine, with the proviso that $R^{11}$ and $R^{12}$ cannot both be hydroxy;
$R^4$ is hydrogen, $C_{1-10}$-alkyl, $C_{3-7}$-cycloalkyl, or phenyl;
$R^A$ is $R^{13}$, F, Cl, Br, I, $NO_2$, $NR^{13}R^{14}$, $NHCOR^{13}$, CN, $COOR^{13}$, $OR^{13}$, $SCH_3$ or $SO_2NR^{11'}R^{12'}$, wherein $R^{13}$ and $R^{14}$ each is hydrogen or $C_{1-6}$-alkyl, and wherein there are 1–2 identical or different $R^A$'s and wherein $R^{11'}$ and $R^{12'}$ can be the same or different and each is H or alkyl, or together $R^{11'}$ and $R^{12'}$ form a saturated heterocyclic group as defined for $R^{11}$ and $R^{12}$; and
$R^9$ is H;
with the proviso that $R^A$ does not represent hydrogen when $R^{11}$ and $R^{12}$ are each hydrogen or $C_{1-3}$ alkyl, when X is oxygen or sulfur and when $R^4$ is hydrogen, $C_{1-5}$-alkyl or phenyl.

2. A β-carbolin-3-carboxylic acid derivative of claim 1, wherein the A-ring has 1–2 RA's.

3. N-methyl-β-carbolin-3-carboxamide.

4. N',N'-(dimethyl)-β-carbolin-3-hydrazide, a compound of claim 1.

5. A pharmaceutical composition comprising an amount of a compound of claim 1 effective as a tranquilizer and a pharmaceutically acceptable carrier.

6. A method of inducing a tranquilizing effect in a patient in need of such treatment which comprises administering to the patient an amount of a compound of claim 1 effective as a tranquilizer.

7. A compound of claim 1 wherein $R^{11}$ and $R^{12}$ are each one of the groups (i) through (iv), groups (iii) through (iv) optionally substituted as defined for claim 1; or form pyrrolidine, piperidine, 3-methoxycarbonyl-piperidine, 4-hydroxy-3-ethoxycarbonylpiperidine, or N-methyl-piperazine.

8. A compound of claim 1, wherein one of $R^{11}$ and $R^{12}$ is a group (v) and the other is a group (i) through (iv), and wherein when one of $R^{11}$ and $R^{12}$ is one of groups (iii) through (iv), said group is optionally substituted as defined for claim 1.

9. A compound of claim 1, wherein:
X is oxgyen,
$R^4$ is H or $C_{1-10}$-alkyl; and
when $R^A$ is $SO_2NR^{11'}R^{12'}$, $R^{11'}$ and $R^{12'}$ can be the same or different and are hydrogen, $C_{1-10}$-alkyl or one of pyrrolidine, piperidine, 3-methoxycarbonyl-piperidine, 4-hydroxy-3-ethoxycarbonylpiperidine, or N-methyl-piperazine.

10. A β-carboline-3-carboxylic acid derivative of the formula

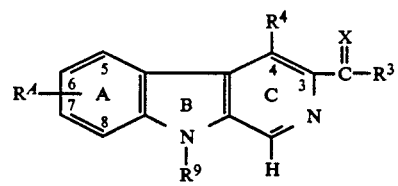

wherein:
X is oxygen, sulphur or $NR^{10}$, wherein $R^{10}$ is hydrogen or alkyl;
$R^3$ is $NR^{11}R^{12}$, wherein $R^{11}$ and $R^{12}$ are the same or different and each is (i) hydrogen, (ii) hydroxy, (iii) $C_{1-10}$-alkyl, (iv) $C_{3-7}$-cycloalkyl, or each of groups (iii)–(iv) optionally substituted with hydroxy, carboxamido, or carboxy, or (v) amino optionally substituted with $C_{1-10}$-alkyl, or wherein $R^{11}$ and $R^{12}$ together with the connecting nitrogen atom form a saturated 5-membered heterocyclic ring or a saturated 6-membered heterocyclic ring, optionally containing one additional N or one O atom, and optionally substituted with a ethoxycarbonyl or methoxycarbonyl group, hydroxy or N-methyl with the proviso that $R^{11}$ and $R^{12}$ cannot both be hydroxy; is hydrogen, $C_{1-10}$-alkyl, $C_{3-7}$-cycloalkyl, or phenyl; is $R^{13}$, F, Cl, Br, I, $NO_2$, $NR^{13}R^{14}$, $NHCOR^{13}$, CN, $COOR^{13}$, $OR^{13}$, $SCH_3$ or $SO_2NR^{11'}R^{12'}$, wherein $R^{13}$ and $R^{14}$ each is hydrogen or $C_{1-6}$-alkyl, and wherein there are 1-2 identical or different $R^4$'s and wherein $R^{11'}$ and $R^{12'}$ can be the same or different and each is H or alkyl, or together $R^{11'}$ and $R^{12'}$ form a saturated heterocyclic group as defined for $R^{11}$ and $R^{12}$; and $R^9$ is H;

with the proviso that $R^{11}$ and $R^{12}$ are not both hydrogen, when X is oxygen and when $R^4$, $R^4$ and $R^9$ each is hydrogen; and that one of $R^{11}$ and $R^{12}$ is not hydrogen when the other is amino and when X is oxygen and $R^4$, $R^4$ and $R^9$ each are hydrogen, and further wherein the A-ring has one or two $R^4$'s, and $R^4$ is 5-cyano.

11. A β-carboline-3-carboxylic acid derivative of claim 10, wherein $R^{11}$ and $R^{12}$ together with the connecting nitrogen atom form pyrrolidine, piperidine, 3-methoxycarbonylpiperidine, 4-hydroxy-3-ethoxycarbonylpiperidine, or N-methyl-piperazine.

12. A β-carboline-3-carboxylic acid derivative of claim 10, wherein X is oxygen.

13. A β-carboline-3-carboxylic acid derivative of claim 1, wherein X is oxygen.

14. A β-carboline-3-carboxylic acid derivative of claim 1, wherein at least one of $R^{11}$ and $R^{12}$ is amino optionally substituted with $C_{1-10}$-alkyl.

15. A β-carboline-3-carboxylic acid derivative of claim 1, wherein $R^{11}$ and $R^{12}$ together with the connecting nitrogen atom form pyrrolidine, piperidine, piperidine-3-methoxycarbonyl, piperidine-4-hydroxy-3-ethoxycarbonyl, or N-methyl-piperazine.

* * * * *